United States Patent
Hacia et al.

(10) Patent No.: US 11,065,247 B2
(45) Date of Patent: Jul. 20, 2021

(54) COMPOSITIONS AND METHODS FOR THE TREATMENT OF ZELLWEGER SPECTRUM DISORDER

(71) Applicants: Joseph Hacia, Los Angeles, CA (US); Nancy E. Braverman, Los Angeles, CA (US); Patricia Dranchak, Los Angeles, CA (US); James Inglese, Los Angeles, CA (US)

(72) Inventors: Joseph Hacia, Los Angeles, CA (US); Nancy E. Braverman, Los Angeles, CA (US); Patricia Dranchak, Los Angeles, CA (US); James Inglese, Los Angeles, CA (US)

( * ) Notice: Subject to any disclaimer, the term of this patent is extended or adjusted under 35 U.S.C. 154(b) by 0 days.

(21) Appl. No.: 16/417,167

(22) Filed: May 20, 2019

(65) Prior Publication Data

US 2020/0046693 A1    Feb. 13, 2020

Related U.S. Application Data

(63) Continuation of application No. 15/623,333, filed on Jun. 14, 2017, now abandoned.

(60) Provisional application No. 62/350,139, filed on Jun. 14, 2016, provisional application No. 62/355,247, filed on Jun. 27, 2016.

(51) Int. Cl.
*A61K 31/485* (2006.01)
*C12Q 1/6883* (2018.01)

(52) U.S. Cl.
CPC .......... *A61K 31/485* (2013.01); *C12Q 1/6883* (2013.01); *C12Q 2600/156* (2013.01)

(58) Field of Classification Search
CPC ................ A61K 31/485; C12Q 1/6883; C12Q 2600/156
See application file for complete search history.

(56) References Cited

PUBLICATIONS

Rizzo (ULF News, Jul. 16-17, 2015) (Year: 2015).*
PubChem (https://pubchem.ncbi.nlm.nih.gov/substance/24278045/version/1#section=Top, Version 1, Jul. 30, 2007). (Year: 2007).*
Patel et al. (IJARPB, 2014, 4(1), 1-6). (Year: 2014).*

* cited by examiner

*Primary Examiner* — Umamaheswari Ramachandran
(74) *Attorney, Agent, or Firm* — Foley & Lardner LLP

(57) ABSTRACT

Provided herein are methods of treating Zellweger spectrum disorder (ZSD) in a subject in need thereof or improving peroxisome assembly in a cell in need thereof comprising administering to the subject a therapeutically effective amount of Compounds of Formula I or II.

16 Claims, 11 Drawing Sheets

COMPOSITIONS AND METHODS FOR THE TREATMENT OF ZELLWEGER SPECTRUM DISORDER

CROSS-REFERENCE TO RELATED PATENT APPLICATIONS

This application is a continuation of application Ser. No. 15/623,333, filed Jun. 14, 2017, which claims priority under 35 U.S.C. § 119(e) to U.S. Provisional Application Nos. 62/350,139 and 62/355,247, filed on Jun. 14, 2016 and Jun. 27, 2016, respectively, the content of each of which are incorporated herein by reference in their entirety.

STATEMENT AS TO FEDERALLY SPONSORED RESEARCH

This invention was made with government support under Grant No. 1ZIATR000052-01, awarded by the National Institutes of Health (NIH). The government has certain rights in the invention.

BACKGROUND

Zellweger spectrum disorder (ZSD) is a disease continuum caused by PEX gene mutations that result in abnormal peroxisome assembly, structure, and function. While those on severe end of the spectrum are born with multiple congenital abnormalities, most patients have a milder, but progressive, disease that typically result in intellectual disabilities, vision and hearing loss, liver dysfunction, decreased bone density, kidney stones, and thin enamel. To date, treatment options are palliative in nature and no targeted therapies exist that directly address peroxisome dysfunction in patients with ZSD.

Peroxisome biogenesis disorders (PBDs) are a spectrum of autosomal recessive disorders caused by defects in specific subset of PEX genes required for the assembly of peroxisomes and their normal abundance, structure, and biochemical functions [1-3]. Approximately 80% of PBD patients fall within the category of Zellweger spectrum disorder (ZSD), which has an overall incidence of approximately 1 in 50,000 births in North America [4]. Severely affected newborns have congenital malformations of the brain and do not survive past infancy; however, most ZSD patients have milder forms of disease that typically result in intellectual disabilities and progressive vision and hearing loss, liver dysfunction, osteopenia, kidney stones, and enamel hypoplasia [5-7]. While this is compatible with longer-term survival, sometimes into adulthood, milder disease can progress to complete hearing and visual loss later in life and patients are at risk for leukodystrophy [5-7]. Current treatment options are palliative in nature [5-7] and thus, there is a need to develop targeted therapies that address the peroxisome assembly defects responsible for disease development and progression.

SUMMARY

A cell-image-based high-content screening (HCS) assay was previously developed to identify small molecules that enhance peroxisome assembly in immortalized skin fibroblasts obtained from a PBD-ZSD patient compound heterozygous for the common hypomorphic PEX1-p.G843D and null PEX1-p.I700fs mutations [8]. The PEX1-p.G843D allele, present in about 30% of the patient population, encodes a misfolded and unstable PEX1 protein with partial activity. Consistent with this residual activity, the presence of at least one PEX1-p.G843D allele is more predictive of a milder disease course than the presence of two null PEX1 alleles [9-11]. Therefore, this assays system is relevant to more mildly effected ZSD patients who could benefit from therapies that address disease progression. To track peroxisome assembly, these patient fibroblasts were engineered to express a reporter green fluorescent protein (GFP) harboring a C-terminal peroxisome targeting sequence 1 (GFP-PTS1) that is imported into the peroxisome matrix in cells from healthy donors, but is primarily cytoplasmic in this system. In principle, this assay can identify small molecules that act by any mechanism that result in a rescue of peroxisome assembly. Thus, in one aspect this disclosure provides a transformed fibroblast (having at least one PEX1-p.G843D allele (which is more predictive of a milder disease course) or a fibroblast having two null PEX1 alleles), transformed to express a reporter protein such as GFP, fused to a C-terminal terminal peroxisome targeting sequence 1 (GFP-PTS) and its use to track peroxisome assembly. In one aspect the cell is a mammalian cell, e.g., a simian cell, a rat cell, a murine cell or a human cell. In a further aspect is a cultured fibroblast or a primary fibroblast. In a yet further aspect, the cells are ZSD patient-derived skin fibroblasts. These cells are useful in an assay to identify molecules and agents that enhance peroxisome assembly in the cells.

This cell-based GFP-PTS1 assay has been applied in a pilot HCS of over 2,000 small molecules at a single concentration [8]. Four small molecules that enhance peroxisome assembly in these patient cells were uncovered with three confirmed using independent assays [8]. The verified hits included a flavonoid and protein kinase C inhibitor, both of which were previously shown to bind the ATP binding site of ABC transporter proteins. Based on prior studies involving other related proteins [12, 13], it was suggested a mechanism for their action as a pharmacological chaperone, binding to the ATP binding sites in the AAA protein, PEX1-p.G843D [8]. Coupled with prior observations that PEX1-p.G843D is a temperature-sensitive allele and responds to other potential molecular chaperones [9, 14], it was proposed that the misfolded PEX1-p.G843D allele protein is amenable to molecular chaperone therapy. Building upon the results of this study, an ongoing clinical trial is testing the effectiveness of one molecular chaperone, betaine, for the treatment of PBD-ZSD [7]. Nevertheless, small molecule therapies applicable to patients homozygous for null PEX gene alleles have not been reported.

The cell-based GFP-PTS1 assay was adapted for the quantitative cell-image-based high-content screening (qHCS) in miniaturized 1536-well format of the Sigma LOPAC1280 collection of pharmacologically active agents for small molecules that improve peroxisome assembly. Compounds showing activity in the initial screen were subject to follow-up validation using cell imaging, biochemical, and protein processing assays. Brain-permeable small molecules that could rescue peroxisomal activities in cultured cells homozygous for null PEX gene alleles were identified. Thus, without being bound by theory, these results identify small molecules that promote the rescue of peroxisome assembly in cells with two PEX1 null alleles, which are also potential reagents for investigating mechanistic aspects of peroxisome biology and developing targeted therapies applicable to an extended group of patients with ZSD.

In more detail, a quantitative cell image-based high content screening (qHCS) assay in 1536-well format was applied to screen the LOPAC 1280 collection of pharmacologically active agents for small molecules that improve peroxisome assembly in ZSD patient-derived skin fibroblasts harboring the common PEX1-p.G843D hypomorphic and PEX1-p.I700fs null alleles. This library was screened at seven concentrations, consistently obtained Z-factors of 0.4, and demonstrated sensitivity by identifying the previously known flavonoid apigenin as a bioactive molecule. A novel group of compounds active the micromolar range and rescued peroxisome functions in patient cells based on cell imaging, biochemical, and protein processing assays was uncovered. Two compounds, naltriben and naltrindole, are opioid receptor antagonists known cross the blood-brain-barrier in rodents. Naltriben is the first reported molecule to reduce very long chain fatty acid levels in patient cells two PEX1 null alleles. Overall, the novel bioactive small molecules identified can provide tools for investigating peroxisome biogenesis and provide for the development of targeted small molecule therapies for PBD-ZSD and common diseases associated with peroxisome dysfunction.

Accordingly, in one aspect, provided herein is a method of treating Zellweger spectrum disorder and/or diseases associated with peroxisome dysfunction in a subject in need thereof, the method comprising, or alternatively consisting essentially of, or yet further consisting of, administering to the subject a therapeutically effective amount of a compound of Formula I:

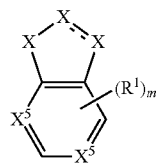

Formula I or a tautomer thereof, or a pharmaceutically acceptable salt of each of the foregoing, or an N-oxide of each of the foregoing, or a pharmaceutically acceptable solvate of each of the foregoing,
wherein:
⫽ is a single or a double bond;
X is $NR^2$ or $CR^5R^5$ when ⫽ is a single bond or X is N or $CR^5$ when ⫽ is a double bond;
$X^5$ is N or $CR^5$, provided that at least one of X and $X^5$ is N or $NR^2$;
each $R^2$ independently is H, an optionally substituted $C_1$-$C_8$ alkyl, an optionally substituted $C_1$-$C_8$ alkoxy, or an optionally substituted $C_2$-$C_8$ alkenyl;
each $R^5$ independently is H, an optionally substituted $C_1$-$C_8$ alkyl, an optionally substituted $C_1$-$C_8$ alkoxy, an optionally substituted $C_2$-$C_8$ alkenyl, an optionally substituted $=NR^6$, or an optionally substituted $—NR^{20}R^{30}$;
each $R^1$ independently is H, an optionally substituted $C_1$-$C_8$ alkyl, an optionally substituted $C_1$-$C_8$ alkoxy; or an optionally substituted $—NR^{20}R^{30}$;
each $R^{20}$ and $R^{30}$ independently is H, an optionally substituted $C_1$-$C_8$ alkyl, an optionally substituted $C_1$-$C_8$ alkoxy, an optionally substituted 5-10 membered aryl, an optionally substituted 5-10 membered heteroaryl; an optionally substituted 3-10 membered cycloalkyl, or an optionally substituted 5-10 membered heterocyclyl;
each $R^6$ independently is H, an optionally substituted $C_1$-$C_8$ alkyl, an optionally substituted $C_1$-$C_8$ alkoxy, or hydroxy; and
m is 0, 1, or 2.

In one aspect, the subject has at least one PEX1-p.G843D allele, and in another aspect, the subject has two null PEX1 alleles.

In one aspect, provided herein is a method of treating Zellweger spectrum disorder and/or diseases associated with peroxisome dysfunction in a subject in need thereof, the method comprising or alternatively consisting essentially of, or yet further consisting of, administering to the subject a therapeutically effective amount of a compound of Formula II:

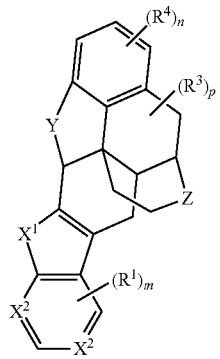

Formula II or a tautomer thereof, or a pharmaceutically acceptable salt of each of the foregoing, or an N-oxide of each of the foregoing, or a pharmaceutically acceptable solvate of each of the foregoing, wherein:
$X^1$ is O, S, or $NR^2$;
$X^2$ is N or $CR^5$;
each $R^1$ independently is H, an optionally substituted $C_1$-$C_8$ alkyl, an optionally substituted $C_1$-$C_8$ alkoxy; or an optionally substituted $—NR^{20}NR^{30}$;
each $R^2$ independently is H, an optionally substituted $C_1$-$C_8$ alkyl, an optionally substituted $C_1$-$C_8$ alkoxy, or an optionally substituted $C_2$-$C_8$ alkenyl;
each $R^5$ independently is H, an optionally substituted $C_1$-$C_8$ alkyl, an optionally substituted $C_1$-$C_8$ alkoxy, an optionally substituted $C_2$-$C_8$ alkenyl, an optionally substituted $=NR^6$, or an optionally substituted $—NR^{20}R^{30}$;
each $R^{20}$ and $R^{30}$ independently is H, an optionally substituted $C_1$-$C_8$ alkyl, an optionally substituted $C_1$-$C_8$ alkoxy, an optionally substituted 5-10 membered aryl, an optionally substituted 5-10 membered heteroaryl, an optionally substituted 3-10 membered cycloalkyl, or an optionally substituted 5-10 membered heterocyclyl;
each $R^3$ and $R^4$ independently is H, an optionally substituted $C_1$-$C_8$ alkyl, an optionally substituted $C_1$-$C_8$ alkoxy; an optionally substituted $C_2$-$C_8$ alkenyl, or a hydroxy;
Y and Z independently is O, S, or $NR^2$;
n is 0, 1, 2, or 3;
m is 0, 1, or 2; and
p is 0, 1, 2, or 3. In one aspect, the subject has at least one PEX1-p.G843D allele, and in another aspect, the subject has two null PEX1 alleles. The subject can be a mammal, for example a human patient.

In one aspect, provided herein is a method of treating Zellweger spectrum disorder and/or diseases associated with peroxisome dysfunction in a subject in need thereof, the method comprising, or alternatively consisting essentially of, or yet further consisting of, administering to the subject a therapeutically effective amount of a compound of Table 3, or a tautomer thereof, or a pharmaceutically acceptable salt of each of the foregoing, or an N-oxide of each of the foregoing, or a pharmaceutically acceptable solvate of each of the foregoing. In one aspect, the subject has at least one PEX1-p.G843D allele, and in another aspect, the subject has two null PEX1 alleles. The subject under treatment can be a mammal, for example a human patient.

In one aspect, provided herein is a method of improving peroxisome assembly in a cell in need thereof, the method comprising, or alternatively consisting essentially of, or yet further consisting of, administering to the cell a therapeutically effective amount of a compound of Formula I:

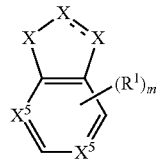

Formula I or a tautomer thereof, or a pharmaceutically acceptable salt of each of the foregoing, or an N-oxide of each of the foregoing, or a pharmaceutically acceptable solvate of each of the foregoing, wherein:

⫽ is a single or a double bond;

X is $NR^2$ or $CR^5R^5$ when ⫽ is a single bond or X is N or $CR^5$ when ⫽ is a double bond;

$X^5$ is N or $CR^5$, provided that at least one of X and $X^5$ is N or $NR^2$;

each $R^2$ independently is H, an optionally substituted $C_1$-$C_8$ alkyl, an optionally substituted $C_1$-$C_8$ alkoxy, or an optionally substituted $C_2$-$C_8$ alkenyl;

each $R^5$ independently is H, an optionally substituted $C_1$-$C_8$ alkyl, an optionally substituted $C_1$-$C_8$ alkoxy, an optionally substituted $C_2$-$C_8$ alkenyl, an optionally substituted =$NR^6$, or an optionally substituted —$NR^{20}R^{30}$;

each $R^1$ independently is H, an optionally substituted $C_1$-$C_8$ alkyl, an optionally substituted $C_1$-$C_8$ alkoxy; or an optionally substituted —$NR^{20}R^{30}$;

each $R^{20}$ and $R^{30}$ independently is H, an optionally substituted $C_1$-$C_8$ alkyl, an optionally substituted $C_1$-$C_8$ alkoxy, an optionally substituted 5-10 membered aryl, an optionally substituted 5-10 membered heteroaryl; an optionally substituted 3-10 membered cycloalkyl, or an optionally substituted 5-10 membered heterocyclyl;

each $R^6$ independently is H, an optionally substituted $C_1$-$C_8$ alkyl, an optionally substituted $C_1$-$C_8$ alkoxy, or hydroxy; and m is 0, 1, or 2.

In one aspect, the cell has at least one PEX1-p.G843D allele, and in another aspect, the cell has two null PEX1 alleles. In one aspect the cell is a mammalian cell, e.g. a human cell. In a further aspect, the cell is a fibroblast, e.g., a human fibroblast.

In one aspect, provided herein is a method of improving peroxisome assembly in a cell in need thereof comprising administering to the cell a therapeutically effective amount of a compound of Formula II:

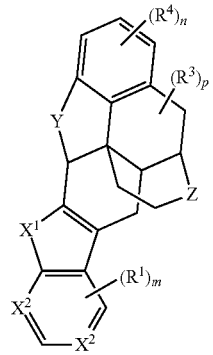

Formula II or a tautomer thereof, or a pharmaceutically acceptable salt of each of the foregoing, or an N-oxide of each of the foregoing, or a pharmaceutically acceptable solvate of each of the foregoing, wherein:

$X^1$ is O, S, or $NR^2$;

$X^2$ is N or $CR^5$;

each $R^1$ independently is H, an optionally substituted $C_1$-$C_8$ alkyl, an optionally substituted $C_1$-$C_8$ alkoxy; or an optionally substituted —$NR^{20}NR^{30}$;

each $R^2$ independently is H, an optionally substituted $C_1$-$C_8$ alkyl, an optionally substituted $C_1$-$C_8$ alkoxy, or an optionally substituted $C_2$-$C_8$ alkenyl;

each $R^5$ independently is H, an optionally substituted $C_1$-$C_8$ alkyl, an optionally substituted $C_1$-$C_8$ alkoxy, an optionally substituted $C_2$-$C_8$ alkenyl, an optionally substituted =$NR^6$, or an optionally substituted —$NR^{20}R^{30}$;

each $R^{20}$ and $R^{30}$ independently is H, an optionally substituted $C_1$-$C_8$ alkyl, an optionally substituted $C_1$-$C_8$ alkoxy, an optionally substituted 5-10 membered aryl, an optionally substituted 5-10 membered heteroaryl, an optionally substituted 3-10 membered cycloalkyl, or an optionally substituted 5-10 membered heterocyclyl;

each $R^3$ and $R^4$ independently is H, an optionally substituted $C_1$-$C_8$ alkyl, an optionally substituted $C_1$-$C_8$ alkoxy; an optionally substituted $C_2$-$C_8$ alkenyl, or a hydroxy;

Y and Z independently is O, S, or $NR^2$;

n is 0, 1, 2, or 3;

m is 0, 1, or 2; and p is 0, 1, 2, or 3.

In one aspect, the cell has at least one PEX1-p.G843D allele, and in another aspect, the cell has two null PEX1 alleles. In one aspect, the cell is a mammalian cell, e.g. a human cell. In a further aspect, the cell is a fibroblast, e.g., a human fibroblast.

In one aspect, provided herein is a method of improving peroxisome assembly in a cell in need thereof, the method comprising, or alternatively consisting essentially of, or yet further consisting of, administering to the cell a therapeutically effective amount of a compound of Table 3, or a tautomer thereof, or a pharmaceutically acceptable salt of each of the foregoing, or an N-oxide of each of the foregoing, or a pharmaceutically acceptable solvate of each of the foregoing. In one aspect, the cell has at least one PEX1-p.G843D allele, and in another aspect, the cell has two null PEX1 alleles. In one aspect the cell is a mammalian cell, e.g., a human cell. In a further aspect, the cell is a fibroblast, e.g., a human fibroblast.

BRIEF DESCRIPTION OF THE DRAWINGS

FIG. 5A: Relative sVLCFA levels, as indicated by the C26:C22:0 LPC ratios (y-axis), for patient cells treated with 0.1% vehicle control, 30 uM diosmetin, or 30 uM naltriben for 5 days (5D) and 10 days (10D). Patient genotypes are provided. FIG. 5B: % C26:0 levels (y-axis) for patient cells treated as indicated in FIG. 5A.

FIG. 7A: Immunostaining with antibodies against peroxisomal membrane protein PMP70 (green) and peroxisomal matrix protein catalase (red). FIG. 7B: Immunostaining with antibodies against peroxisomal membrane protein PMP70 (green) and peroxisomal matrix protein thiolase (red). In all panels, blue indicates DAPI nuclear counterstaining.

DETAILED DESCRIPTION

Figure 1A:
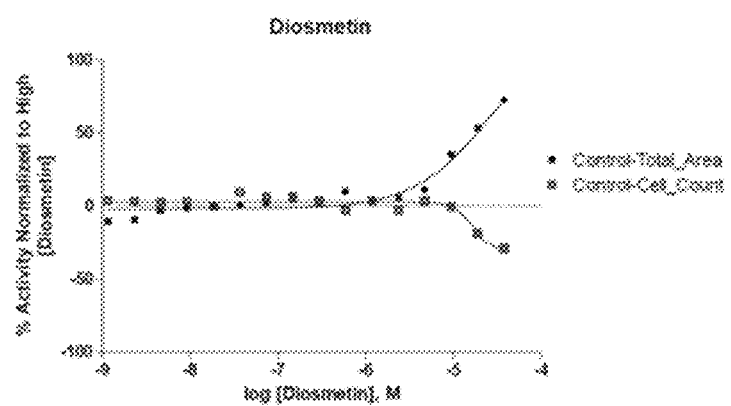
FIGS. 1A-1B: performance of positive chemical control diosmetin in HCS of LOPAC1280 library. A. Relative area of punctate structures in treated ZSD patient-derived assay cells (black) is plotted along with the relative total number of cells, estimated by nuclei count, in each well against diosmetin concentration. B. Data from all plates used in the HCS screening assay are provided.

Throughout this disclosure, various publications, patents and published patent specifications are referenced by an identifying citation. The disclosures of these publications, patents and published patent specifications are hereby incorporated by reference into the present disclosure in their entirety to more fully describe the state of the art to which this invention pertains.

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, $2^{nd}$ edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (R. I. Freshney, ed. (1987)).

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkenyl" refers to monovalent straight or branched hydrocarbyl groups having from 2 to 6 carbon atoms and preferably 2 to 4 carbon atoms and having at least 1 and preferably from 1 to 2 sites of vinyl (—C=C—) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic unsaturation. Examples of such alkynyl groups include acetylenyl (—C≡CH), and propargyl (—CH$_2$C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)— or —CH(CH$_3$)CH$_2$—), butylene (—CH$_2$CH$_2$CH$_2$CH$_2$—), isobutylene (—CH$_2$CH(CH$_3$)CH$_2$—), sec-butylene (—CH$_2$CH$_2$(CH$_3$)CH—), and the like. Similarly, "alkenylene" and "alkynylene" refer to an alkylene moiety containing respective 1 or 2 carbon carbon double bonds or a carbon carbon triple bond.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups, or having from 1-3 carbon atoms replaced with —O—, —S—, or —NR$^Q$— moieties where R$^Q$ is H or C$_1$-C$_6$ alkyl. It is to be noted that when the alkylene is substituted by an oxo group, 2 hydrogens attached to the same carbon of the alkylene group are replaced by "=O". "Substituted alkenylene" and "substituted alkynylene" refer to alkenylene and substituted alkynylene moieties substituted with substituents as described for substituted alkylene.

"Heteroalkylene" refers to an alkylene group wherein one or more carbons is replaced with —O—, —S—, SO$_2$, —NR$^Q$—,

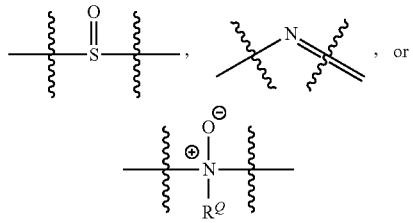

moieties where R$^Q$ is H or C$_1$-C$_6$ alkyl.

"Heteroalkenylene" refers to an alkenylene group wherein one or more carbons is replaced with —O—, —S—, SO$_2$, —NR$^Q$—,

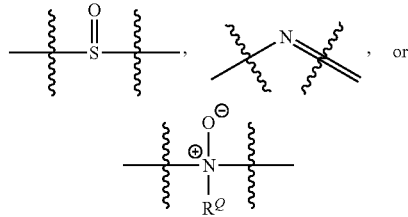

moieties where $R^Q$ is H or $C_1$-$C_6$ alkyl.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{47}$C(O)alkyl, —$NR^{47}$C(O)substituted alkyl, —$NR^{47}$C(O)cycloalkyl, —$NR^{47}$C(O)substituted cycloalkyl, —$NR^{47}$C(O)cycloalkenyl, —$NR^{47}$C(O)substituted cycloalkenyl, —$NR^{47}$C(O) alkenyl, —$NR^{47}$C(O)substituted alkenyl, —$NR^{47}$C(O)alkynyl, —$NR^{47}$C(O)substituted alkynyl, —$NR^{47}$C(O)aryl, —$NR^{47}$C(O)substituted aryl, —$NR^{47}$C(O)heteroaryl, —$NR^{47}$C(O)substituted heteroaryl, —$NR^{47}$C(O)heterocyclic, and —$NR^{47}$C(O)substituted heterocyclic wherein $R^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

An animal, subject or patient for diagnosis or treatment refers to an animal such as a mammal, or a human, ovine, bovine, feline, canine, equine, simian, etc. Non-human animals subject to diagnosis or treatment include, for example, simians, murine, such as, rat, mice, canine, leporid, livestock, sport animals, and pets.

"Amino" refers to the group —$NH_2$.

"Aminosulfonyl" refers to the group —$SO_2NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—$SO_2NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Arylene" refers to a divalent aromatic carbocyclic group of from 6 to 14 carbon atoms having a single ring or multiple condensed rings. "Substituted arylene" refers to an arylene having from 1 to 5, preferably 1 to 3, or more preferably 1 to 2 substituents as defined for aryl groups.

"Heteroarylene" refers to a divalent aromatic group of from 1 to 10 carbon atoms and 1 to 4 heteroatoms selected from the group consisting of oxygen, nitrogen and sulfur within the ring. "Substituted heteroarylene" refers to heteroarylene groups that are substituted with from 1 to 5, preferably 1 to 3, or more preferably 1 to 2 substituents selected from the group consisting of the same group of substituents defined for substituted aryl.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the group —C(O)(O)-alkyl, —C(O)(O)-substituted alkyl, —C(O)O-alkenyl, —C(O)(O)-substituted alkenyl, —C(O)(O)-alkynyl, —C(O)(O)-substituted alkynyl, —C(O)(O)-aryl, —C(O)(O)-substituted-aryl, —C(O)(O)-cycloalkyl, —C(O)(O)-substituted cycloalkyl, —C(O)(O)-cycloalkenyl, —C(O)(O)-substituted cycloalkenyl, —C(O)(O)-heteroaryl, —C(O)(O)-substituted heteroaryl, —C(O)(O)-heterocyclic, and —C(O)(O)-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)(O)-substituted alkynyl, —O—C(O)O-aryl, —O—C(O)O-substituted-aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

A "composition" as used herein, intends an active agent, such as a compound as disclosed herein and a carrier, inert or active. The carrier can be, without limitation, solid such as a bead or resin, or liquid, such as phosphate buffered saline.

Administration or treatment in "combination" refers to administering two agents such that their pharmacological effects are manifest at the same time. Combination does not require administration at the same time or substantially the same time, although combination can include such administrations.

"Cyano" refers to the group —CN.

"Cycloalkyl" refers to cyclic alkyl groups of from 3 to 10 carbon atoms having single or multiple cyclic rings including fused, bridged, and spiro ring systems. The fused ring can be an aryl ring provided that the non-aryl part is joined to the rest of the molecule. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Cyclopropano" refers to:

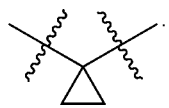 [SMILES: *C1(*)CC1]

"Cyclobutano" refers to:

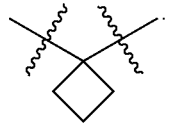

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Certain non-limiting examples include pyridinyl, pyrrolyl, indolyl, thiophenyl, oxazolyl, thizolyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O).

Phenylene refers to a divalent aryl ring, where the ring contains 6 carbon atoms.

Substituted phenylene refers to phenylenes which are substituted with 1 to 4, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

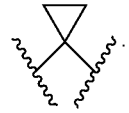

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-SO$_2$—, phenyl-SO$_2$—, and 4-methylphenyl-SO$_2$—.

"Substituted sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —C(=S)—.

"Thioxo" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Optionally substituted" refers to a group selected from that group and a substituted form of that group. Substituted groups are defined herein. In one embodiment, substituents are selected from $C_1$-$C_{10}$ or $C_1$-$C_6$ alkyl, $C_2$-$C_6$ alkenyl, $C_2$-$C_6$ alkynyl, $C_6$-$C_{10}$ aryl, $C_3$-$C_8$ cycloalkyl, $C_2$-$C_{10}$ heterocyclyl, heteroaryl, halo, nitro, cyano, —$CO_2H$ or a $C_1$-$C_6$ alkyl ester thereof.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

It is understood that the above definitions are not intended to include impermissible substitution patterns (e.g., methyl substituted with 5 fluoro groups). Such impermissible substitution patterns are well known to the skilled artisan.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Uracil isostere" refers to an isostere of uracil and does not include uracil or any halouracil. Such a moiety provides some or all of the hydrogen bond acceptor-donor-acceptor property of uracil and optionally provides other structural characteristics of uracil. A skilled artisan will further appreciate the meaning of this term by reading the non limiting examples of such uracil isosteres provided herein.

"Pharmaceutically acceptable salt" refers to salts of a compound, which salts are suitable for pharmaceutical use and are derived from a variety of organic and inorganic counter ions well known in the art and include, when the compound contains an acidic functionality, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "Handbook of Pharmaceutically Acceptable Salts," (2002), Verlag Helvetica Chimica Acta, Zürich, Switzerland), for a discussion of pharmaceutical salts, their selection, preparation, and use.

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkyl sulfonic acids (e.g., methanesulfonic acid, ethanesulfonic acid, 1,2-ethane-di sulfonic acid, 2-hydroxyethanesulfonic acid, etc.), aryl sulfonic acids (e.g., benzenesulfonic acid, 4-chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

As used herein, to "treat" further includes systemic amelioration of the symptoms associated with the pathology and/or a delay in onset of symptoms. Clinical and subclinical evidence of "treatment" will vary with the pathology, the subject and the treatment.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, topical application, intraperitoneal, intravenous, subcutaneous and by inhalation. An agent of the present disclosure can be administered for therapy by any suitable route of administration. It will also be appreciated that the preferred route will vary with the condition and age of the recipient, and the disease being treated.

The compositions of the present disclosure can be used in the manufacture of medicaments and for the treatment of humans and other animals by administration in accordance with conventional procedures, such as an active ingredient in pharmaceutical compositions.

As used herein, the term "patient" or "subject" intends an animal, a mammal or yet further a human patient. For the purpose of illustration only, a mammal includes but is not limited to a human, a feline, a canine, a simian, a murine, a bovine, an equine, a porcine or an ovine. In terms of cells, the term "mammalian cells" includes, but is not limited to cells of the following origin: a human, a feline, a canine, a simian, a murine, a bovine, an equine, a porcine or an ovine.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks.

"Therapeutically effective amount" of a drug or an agent refers to an amount of the drug or the agent that is an amount sufficient to obtain a pharmacological response such as alleviation of symptoms of ZSD and disorders related to peroxisome dysfunction, e.g., peroxisome biogenesis disorders (PBDs) and in one aspect, is an amount of the drug or agent that, when administered to a patient with a specified disorder or disease, is sufficient to have the intended effect, e.g., treatment, alleviation, amelioration, palliation or elimination of one or more manifestations of the specified disorder or disease in the patient. A therapeutic effect does not necessarily occur by administration of one dose, and may occur only after administration of a series of doses. Thus, a therapeutically effective amount may be administered in one or more administrations.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein, the terms "Zellweger spectrum disorder" and "disorders related to peroxisome dysfunction" (e.g. peroxisome biogenesis disorders) refer in general to a group of rare, genetic diseases that present as a spectrum or continuum of diseases. The diseases have overlapping signs and symptoms and affect multiple parts and systems of the body. In some embodiments, the most severe form is Zellweger Syndrome (ZS). Symptoms of Zellweger Syndrome include but are not limited to hypotonia, feeding problems, hearing and vision loss, seizures, distinctive facial characteristics, and skeletal abnormalities. In some embodiments, the intermediate form is neonatal adrenoleukodystrophy. In some embodiments, the least severe form is infantile Refsum disease (IRD). Symptoms of neonatal adrenoleukodystrophy and infantile Refsum disease include but are not limited to hyptonia, vision and/or hearing problems, liver dysfunction, developmental delay, and learning disabilities. Thus, "treating" or "treatment" of Zellweger spectrum disorder and disorders related to peroxisome dysfunction in a patient refer to the delay, amelioration, or slowing of progression of the various symptoms of Zellweger spectrum disorder and related disorders. A treating physician can determine if the symptoms have been delayed ameliorated, or slowed.

MODES FOR CARRYING OUT THE DISCLOSURE

Compound Library

The Sigma Library of Pharmacologically Active Compounds (LOPAC), a chemically library of 1280 compounds, was purchased as 10 mM stock solutions in DMSO. As previously described [15], all compounds were reformatted into 1536-well assay plates with final compound concentrations in a 3 µl assay volume in a 7 point titration ranging from 2.5 nM to 38.4 µM (0.1% DMSO final concentration for all compounds tested). Each assay plate contained the positive 'chemical control' diosmetin present in the 7 point titration and a positive 'genetic control', ZSD patient cells, described below, transduced with PEX1-lentiviral vector present in 7 plate different wells in 0.1% DMSO. Each assay plate also contained a negative 0.1% DMSO vehicle control, final concentration, present in 7 different wells.

High-Content Screening (HCS) and Data Analysis

The cells used in the quantitative HCS are as previously described [8]. Briefly, immortalized human fibroblasts obtained from a ZSD patient compound heterozygous for the hypomorphic PEX1-p.G843D and null PEX1-p.I700fs alleles, expressed the GFP-PTS1 reporter protein. Primary and immortalized skin fibroblasts were grown for 72 hours at 37° C. with 5% CO2 and 90% relative humidity (RH) in fibroblast growth medium [16, 17] prior to distributing to sample wells in 1536-well format. After incubating for two days at 37° C. with 5% CO2 and 90% RH prior to staining with DAPI and data analysis, there was an average of 577±44 cells per well.

A detailed assay protocol is provided in Table 1. Briefly, the GE INCell Analyzer 2000 high-content imaging system was used to acquire data with a 20×/0.45 ELWD Plan Fluor objective with excitation wavelengths DAPI (350 nm) and FITC (495 nm), and emission wavelengths DAPI (470 nm) and FITC (520 nm) to image the DAPI-stained nuclei and GFP-labeled PTS1, respectively. Estimates of the percentage of positively responding cells in a well were based on the average total cellular area composed of appropriately sized and shaped puncta. Visual inspection by 3 independent observers was employed for data analysis with scoring based on the clarity of the cytoplasmic staining and the appearance of cells with at least 7 distinct punctate cytoplasmic structures consist with peroxisome size and shape. In the latter case, wells showing at least 30% of cells with rescue of peroxisome assembly at the highest compound concentration (38.4 µM) were initially prioritized for further analysis. Prior to data analysis, compounds showing appreciable (at least 30%) rescue at a lower concentration, but no subsequent rescue at the next highest concentration(s) would be discarded as hits unless toxicity was noted at these higher concentrations. In no circumstance did this latter situation occur.

TABLE 1

Hsa PEX1 PBD PTS1-GFP Puncta Assay with Hoechst Nuclear Stain with Genetic
Control Cell Lines Diosmetin Control Treatment - LOPAC Screen

| Sequence | Parameter | Value | Description |
|---|---|---|---|
| 1 | Cells | 6 μl | Seed 300 or 500 cells/well into respective columns of nine black/clear bottom low base, TC plates (Aurora) and nine black/clear bottom high base, collagen coated plates (Corning) - PBD PTS1-GFP cells & PBD CMV_hPEX1 genetically corrected control cells |
| 2 | Incubation | 16 hr | Incubate at 37° C., 5% $CO_2$, 95% RH overnight |
| 3 | Compounds | 23 nl | LOPAC library compounds [high concentration = 10 mM] or vehicle (DMSO); Compound transfer by Pintool (duplicate pinning between two plate types): Control = Diosmetin (10 mM high concentration, 16-pt 1:2 titration) |
| 4 | Incubation | 48 hr | Incubate at 37° C., 5% $CO_2$, 95% RH for 2 days |
| 5 | Fixation | 5 μl | Fix and stain cells with 3.5% PFA + 1:2000 dilution of Hoechst stain for 20 min |
| 6 | Incubation | 20 min | Incubate at room temperature, protected from light |
| 7 | Wash | 10 μl | Wash fixed and stained cells with 1X PBS |
| 8 | Detector | InCell | Read cellular PTS1 green fluorescence (GFP) and Dapi nuclear fluorescence (Hoechst stain) |

Notes 5-7 Cells fixed with 3.5% Paraformaldehyde and nuclei stained with 1:2000 dilution of Hoechst stain solution for 20 min with BioTek EL406 ("Trish Aspirate - 5 μl Dispense" Protocol) on HIRES robot in Building B.
4.7% Paraformaldehyde + 1:1, 480 dilution of Hoechst stain solution prepared (to compensate for 1.76 μl residual volume per well after aspiration):
36.72 ml 32% PFA + 170 μl Hoechst stain + 213.11 ml 1X PBS = 250 ml
Media aspirated off from cells and 5 μl/well 3.5% PFA + Hoechst stain added with BioTek Protocol: "Trish Aspirate - 5 μl Dispense" using 5 μl PFA cassette.
Plates incubated for 20 min at room temperature, protected from light.
PFA and Hoechst Stain removed and plates washed twice with 1X PBS with BioTeck Protocol: "Trish Aspirate - 5 μl Dispense" using 5 μl PFA cassette.
BioTek EL406 Protocol: Aspirate => Travel Rate = 3, Z = 27, 3.4 mm, complete plate selected
Dispense => Volume = 5 μl, Low Flow Rate, Z = 200, 9.14 mm
Predispense = 10 μl/tube, # = 1

8 Read cellular PTS1 green fluorescence, DsRed peroxisomal membrane protein label, and Dapi nuclear stain on GE InCell 2000 (Protocol: "Trish\PBD GFP"): Excitation = Dapi (Hoechst), FITC (GFP); Emission = Dapi (Hoechst), FITC (GFP); 2D-Deconvoluted; Exposure = 0.250, Offset = 8.0 (Hoechst), Exposure = 0.250, Offset = 9.0 (GFP); Laser Autofocus.

Cell Imaging Validation Assays

Primary fibroblast cultures from patients and healthy controls were obtained from the Peroxisomal Disease Laboratory at the Kennedy Krieger Institute and Coriell Institute Cell Repository, respectively. All cells were grown in fibroblast medium [16, 17] at 37° C. with 5% CO2, as described [18]. As required, cells were fixed, permeabilized, and incubated with antiserum as reported [19, 17, 16].

Biochemical Analysis

As previously described [17, 16], relative sVLCFA levels were evaluated in lysates of cultured cells by determining the ratio of C26:0-lysophosphorylcholine and C22:0-lysophosphorylcholine levels (i.e. C26:0LPC/C22:0LPC) by liquid chromatography-tandem mass spectrometry (LC-MS/MS). As used herein, % C26:0LPC is relative to the total amount of all lysophosphatidylcholine (LPC) molecular species (C26:0, C24:0, C22:0, C20:0, C18:0, C18:1, and C18:2 LPCs) and lyso-platelet activating factor molecular species (C16:0-Lyso-PAF, and 1-C18:0-Lyso-PAF) determined in the same LC-MS/MS analysis.

Thiolase Processing Assay

Western blot analysis of peroxisomal thiolase was accomplished as previously described [8]. Rabbit polyclonal anti-ACAA1 (peroxisomal thiolase) antibody (1:7,500 dilution) and rabbit polyclonal anti-GAPDH antibody (AbCam, 1:7, 500 dilution) were used in these analyses. Membranes were visualized by ECL detection agent (GE Healthcare Amersham) and images were processed and quantified by ImageJ software.

Development of a Quantitative High-Content Screening (qHCS)

Building upon prior HSC conducted in 96-well plates [8], a cell image-based quantitative high content screening (qHCS) assay was implemented in a 1536-well plate format for compounds that enhance peroxisome assembly in ZSD patient cells. Immortalized ZD patient-derived skin fibroblasts, harboring common hypomorphic PEX1-p.G843D and null PEX1-p.I700fs mutations, and engineered to express a GFP-PTS1 reporter protein provided the basis for this assay. These PEX1-mutant cells show a cytosolic localization of the GFP-PTS1 reporter in contrast to its peroxisomal localization in cells from healthy donors. Each assay plate contained 7 replicates of a negative vehicle control (0.1% DMSO), a 7 point titration of the positive chemical control diosmetin, and 7 replicates of a positive genetic control (Methods).

Figure 1B:
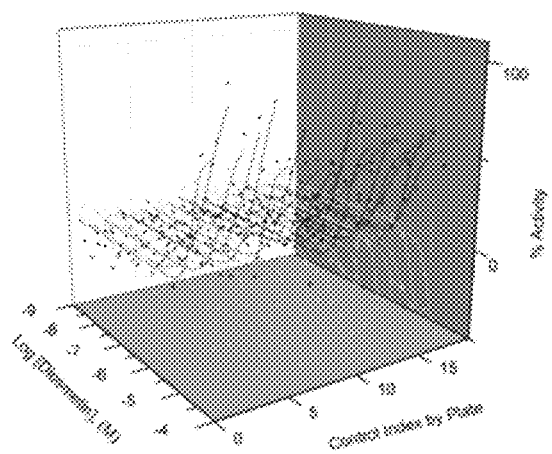

In a 1536-well format, the predominantly cytoplasmic localization of the GFP-PTS1 reporter protein in the ZSD cells and rescue of peroxisome assembly in these same cells when transduced with PEX1-lentiviral delivery system was verified. The consistent appearance of GFP-PTS1-positive puncta, the size and shape of peroxisomes, and clearing of cytoplasmic signals indicated a robust rescue of peroxisome assembly upon treatment with the highest concentration (38.4 μM) of diosmetin. Z-factors of 0.39±0.07 were achieved across all 1536-well assay plates based on data from the negative and positive chemical control (38.4 μM diosmetin). In addition, 7-point titration showed a dose-dependent improvement of peroxisome assembly in diosmetin-treated cells (FIGS. 1A-1B). The positive genetic control cells showed robust rescue, but were not used in subsequent data analysis. Other quality control metrics are provided in Table 2.

TABLE 2

Summary statistics for screening

| Parameters | Assay Parameters | |
|---|---|---|
| | Total Area of Puncta | Cell number (cytotoxicity) based on nuclei count |
| 1536-well plates | 7 (+2 DMSO) | 7 (+2 DMSO) |
| Compounds tested | 1280 | 1280 |
| Points per titration | 7 | 7 |
| Data points | 8960 | 8960 |
| B:I | 3.66 ± 0.17 | NA |
| | DMSO     Diosmetin | |
| Output signal | 34.1 ± 6.3    124.5 ± 12.3 | 577 ± 44 |
| CV | 18.5 ± 2.3    9.9 ± 1.6 | 7.7 ± 2.5 |
| Z' factor | 0.39 ± 0.07 | N/A |

TABLE 2-continued

Summary statistics for screening

| Parameters | Assay Parameters | |
|---|---|---|
| | Total Area of Puncta | Cell number (cytotoxicity) based on nuclei count |
| Control condition 1 | Diosmetin (38.3 uM) | Zero cells |
| Control IC50 (uM) | 13.1 ± 4.5 | N/A |

Identification of Lead Compounds

Lead compounds were identified through quantitative analysis using InCell Analyzer software and by semi-quantitative visual inspection of all wells (Methods). 31 compounds were identified that provided evidence of improved peroxisome assembly in at least 20% of patient cells in a given well at 38.4 µM, the highest concentration tested (Table 3). Background recovery levels were typically less than 5% in this assay. 8 compounds (naltriben methanesulfonate hydrate, actinonin, CGP57380, indirubin-3'-oxime, naltrindole hydrochloride, H-8 dihydrochloride, and apigenin) that showed evidence of assembly rescue in at least 40% of cells were studied (Table 3). The flavonoid apigenin served as another independent positive control since it was previously identified in a prior study as rescuing peroxisome assembly in ZSD patient cells (Braverman et al. in preparation).

TABLE 3

Additional file 3. Compounds promoting rescue of peroxisome assembly in at least 20% of cells in LOPAC screen as judged by visual inspection

| Compound Name | Positive Recovery | No Recovery | Questionable Recovery | Total Number of Cells | % Rescued |
|---|---|---|---|---|---|
| Naltriben methanesulfonate hydrate | 207 | 24 | 2 | 233 | 88.8% |
| Actinonin | 155 | 73 | 6 | 234 | 66.2% |
| CGP 57380 | 252 | 133 | 4 | 389 | 64.8% |
| Indirubin-3'-oxime | 119 | 77 | 5 | 201 | 59.2% |
| Naltrindole hydrochloride | 186 | 135 | 0 | 321 | 57.9% |
| H-8 dihydrochloride | 135 | 106 | 5 | 246 | 54.9% |
| Apigenin | 141 | 118 | 5 | 264 | 53.4% |
| 1-(5-Isoquinolinylsulfonyl)-3-methylpiperazine dihydrochloride | 148 | 163 | 0 | 311 | 47.6% |
| Nifedipine | 95 | 143 | 3 | 241 | 39.4% |
| Bay 11-7085 | 84 | 127 | 4 | 215 | 39.1% |
| BAY 61-3606 hydrochloride hydrate | 123 | 197 | 6 | 326 | 37.7% |
| Pentamidine isethionate salt | 99 | 161 | 4 | 264 | 37.5% |
| Bay 11-7082 | 87 | 144 | 2 | 233 | 37.3% |
| 6-Methylaminopurine 9-ribofuranoside | 127 | 211 | 5 | 343 | 37.0% |
| Leflunomide | 104 | 190 | 9 | 303 | 34.3% |
| 8-(Diethylamino)octyl-3,4,5-trimethoxybenzoate hydrochloride | 81 | 155 | 1 | 237 | 34.2% |
| IRAK-1/4 Inhibitor I | 106 | 213 | 7 | 326 | 32.5% |
| P1,P4-Di(adenosine-5') tetraphosphate ammonium salt | 97 | 204 | 1 | 302 | 32.1% |
| BIO (6-bromoinirubin-3'-oxime) | 121 | 258 | 5 | 384 | 31.5% |
| 1-(5-Isoquinolinylsulfonyl)-2-methylpiperazine dihydrochloride (H-7) | 115 | 261 | 3 | 379 | 30.3% |
| Roscovitine | 49 | 118 | 1 | 168 | 29.2% |
| SP600125 | 66 | 171 | 4 | 241 | 27.4% |
| HA-100 | 68 | 218 | 5 | 291 | 23.4% |
| Ribavirin | 75 | 256 | 2 | 333 | 22.5% |
| Piribedil maleate salt | 83 | 281 | 0 | 364 | 22.8% |
| TBBz | 56 | 202 | 5 | 263 | 21.3% |
| LY-294,002 hydrochloride | 38 | 135 | 0 | 173 | 22.0% |
| Tetracaine hydrochloride | 67 | 251 | 5 | 323 | 20.7% |
| LFM-A13 | 76 | 279 | 1 | 356 | 21.3% |
| N-Acetyltryptamine | 73 | 272 | 2 | 347 | 21.0% |
| Tyrphostin AG 1478 | 67 | 263 | 1 | 331 | 20.2% |

Analysis of Lead Compounds by Cell Imaging

Figure 2:
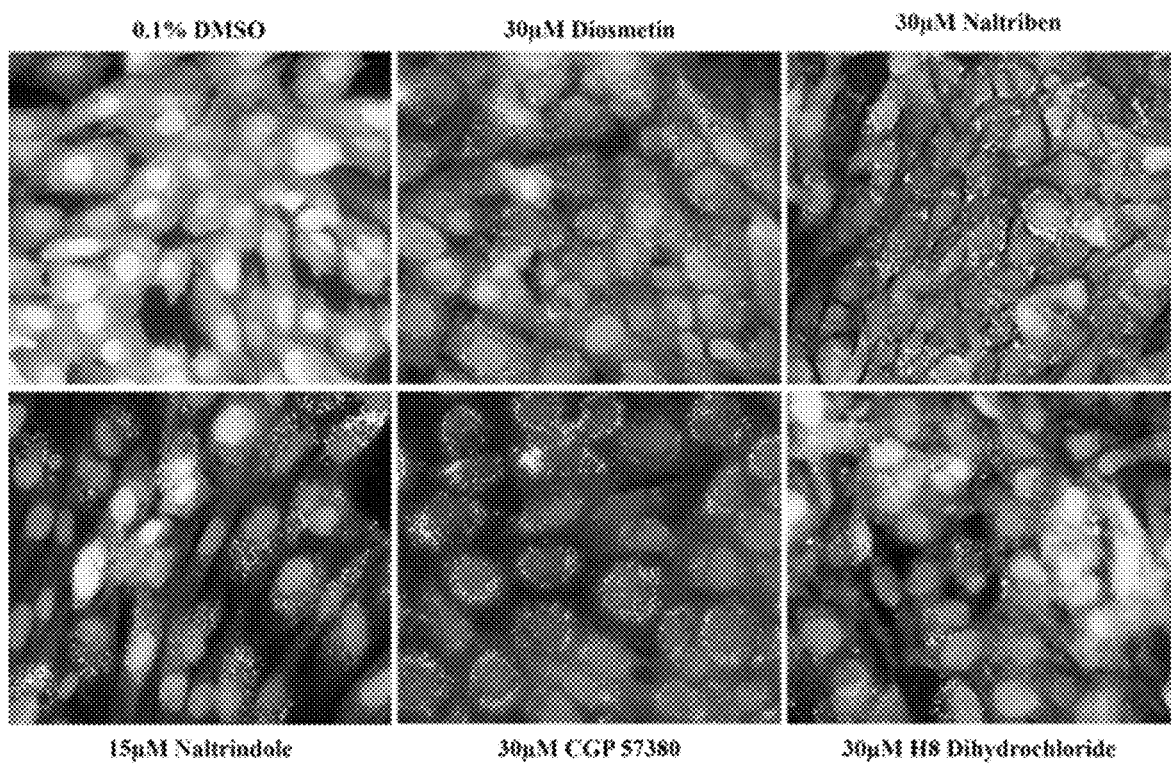
FIG. 2: independent confirmation of activity compounds uncovered in HCS using the GFP-PTS1 expressing reporter cells. Immortalized ZSD patient-derived cells (PEX1-p.G843D/I700fs) expressing GFP-PTS1 reporter were cultured for 10 days at 37° C. in 6-well plates with the compounds at the indicated concentrations and subsequently stained with DAPI to highlight nuclei. 0.1% DMSO is the vehicle control. Punctate structures are indicative of peroxisome assembly.
Figure 3:
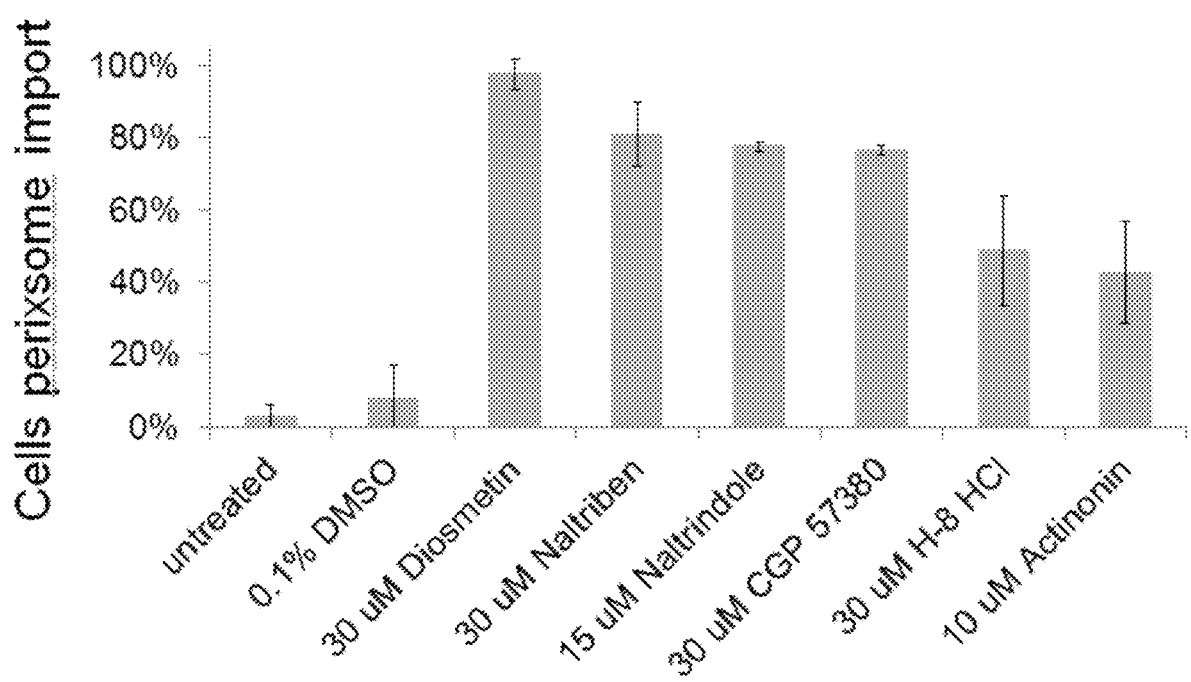
FIG. 3: quantification of peroxisome assembly rescue in GFP-PTS1 expressing reporter cells. Immortalized ZSD patient-derived cells (PEX1-p.G843D/I700fs) expressing GFP-PTS1 reporter were cultured for 5 days at 37° C. in 6-well plates with the compounds at the indicated concentrations and subsequently stained with DAPI to highlight nuclei. 0.1% DMSO is the vehicle control. Punctate structures are indicative of peroxisome assembly. Experiments were conducted a minimal of two times.
Figure 4:
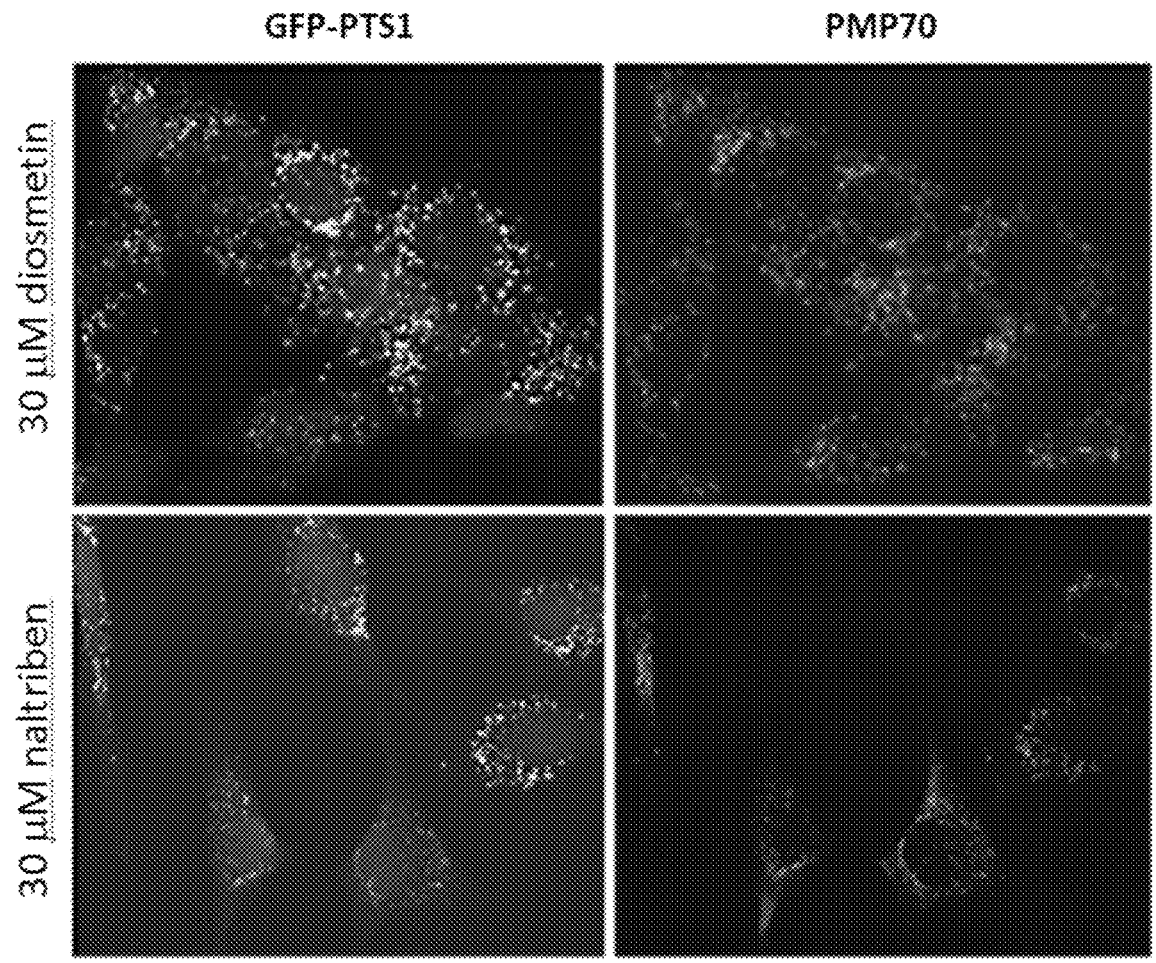
FIG. 4: redistribution of GFP-PTS1 reporter to peroxisome in immortalized fibroblasts (PEX1 p.G843D/I700fs) cultured with chemicals at 5 days. The M2H cells were cultured with 30 µM diosmetin and 30 µM naltriben for 5 days. Cells were fixed and incubated with PMP70 antiserum and rhodamine conjugated secondary antibody. Green: GFP-PTS2 reporter; red: PMP70; blue: DAPI nuclear counterstaining. The co-localization of PMP70 and GFP is evident.

A subset of the most promising compounds was tested in the GFP-PTS1 expressing HCS assay cells grown in 6-well-format, with primary investigations conducted to assess toxicity (Table 4). The structurally similar compounds naltriben methanesulfonate hydrate and naltrindole hydrochloride promoted a reproducible robust rescue of peroxisome assembly when treated at 5 or 10 days with compounds at 30 uM concentration (FIGS. 2-3). The peroxisomal identity of the punctate structures was confirmed by co-staining with antibodies against the peroxisomal membrane protein PMP70 (FIG. 4). Given its structural similarity to naltriben methanesulfonate hydrate and naltrindole hydrochloride, pilot studies of the FDA-approved drug naltrexone [20, 21] were conducted at multiple concentrations for 5 and 10 days and found no cellular rescue of punctate GFP-PTS1 signals or clearing of cytoplasmic GFP-PTS1 staining.

TABLE 4

Additional file 4. Independent confirmatory analysis of hits from chemical screen using cells employed in HCS of LOPAC1280 library

| Chemical Name | Treatment (concentration, time) | Positive Recovery (# of cells) | No Recovery (# of cells) | Questionable Recovery (# of cells) | Number of Cells | Quantification (% rescued) |
|---|---|---|---|---|---|---|
| Naltriben methanesulfonate hydrate | 30 µM, 05 Days | 26 | 23 | 13 | 62 | 52.42% |
| | 30 µM, 05 Days | 167 | 56 | 1 | 224 | 74.78% |
| | 30 µM, 05 Days | 411 | 1 | 239 | 651 | 63.21% |
| | 30 µM, 10 Days | 314 | 7 | 9 | 330 | 96.52% |
| | 30 µM, 10 Days | 775 | 105 | 24 | 904 | 91.54% |
| | 30 µM, 10 Days | 528 | 274 | 158 | 960 | 69.27% |
| Naltrindole hydrochloride | 10 µM, 05 Days | 530 | 8 | 426 | 964 | 55.39% |
| | 10 µM, 05 Days | 155 | 253 | 789 | 1197 | 23.52% |
| | 10 µM, 05 Days | 542 | 6 | 405 | 953 | 57.19% |
| | 10 µM, 05 Days | 427 | 7 | 155 | 589 | 73.09% |
| | 10 µM, 10 Days | 85 | 330 | 22 | 437 | 21.97% |
| | 10 µM, 10 Days | 110 | 340 | 590 | 1040 | 26.92% |
| | 10 µM, 10 Days | 468 | 466 | 1470 | 2404 | 29.16% |
| | 10 µM, 10 Days | 201 | 4 | 644 | 849 | 23.91% |
| | 15 µM, 05 Days | 495 | 5 | 149 | 649 | 76.66% |
| | 15 µM, 05 Days | 1725 | 21 | 469 | 2215 | 78.35% |
| | 15 µM, 10 Days | 587 | 4 | 141 | 609 | 96.72% |
| | 15 µM, 10 Days | 1738 | 44 | 295 | 2077 | 84.74% |
| Naltrexone Hydrochloride | 100 nM, 05 Days | — | — | — | ~250 | <10.00% |
| | 100 nM, 10 Days | — | — | — | ~700 | <10.00% |
| | 10 nM, 05 Days | — | — | — | ~200 | <10.00% |
| | 10 nM, 10 Days | — | — | — | ~700 | <10.00% |
| | 10 µM, 05 Days | — | — | — | ~200 | <10.00% |
| | 10 µM, 10 Days | — | — | — | ~700 | <10.00% |
| | 1 nM, 05 Days | 4 | 247 | 0 | 251 | 1.59% |
| | 1 nM, 10 Days | — | — | — | ~750 | <10.00% |
| | 1 µM, 05 Days | — | — | — | ~200 | <10.00% |
| | 1 µM, 10 Days | — | — | — | ~700 | <10.00% |
| | 30 µM, 05 Days | — | — | — | ~200 | <10.00% |
| | 30 µM, 05 Days | 4 | 6 | 2035 | 2045 | 0.34% |
| | 30 µM, 10 Days | — | — | — | ~700 | <10.00% |
| | 30 µM, 10 Days | 44 | 2 | 2980 | 3026 | 1.49% |
| (R)-Roscovitine | 10 µM, 05 Days | 112 | 10 | 1099 | 1221 | 9.58% |
| | 10 µM, 10 Days | 6 | 189 | 0 | 195 | 3.08% |
| | 10 µM, 10 Days | 860 | 12 | 1416 | 2288 | 37.85% |
| | 15 µM, 05 Days | 96 | 17 | 1166 | 1279 | 8.17% |
| | 15 µM, 10 Days | 722 | 17 | 688 | 1427 | 51.19% |
| LY-294,002 hydrochloride | 10 µM, 05 Days | 158 | 140 | 30 | 328 | 52.74% |
| | 10 µM, 10 Days | 72 | 174 | 24 | 270 | 31.11% |
| | 30 µM, 10 Days | 274 | 6 | 1096 | 1376 | 20.13% |
| 1-(5-Isoquinolinyl-sulfonyl)-3-methylpiperazine dihydrochloride | 10 µM, 05 Days | 16 | 12 | 1568 | 1596 | 1.38% |
| | 10 µM, 10 Days | 92 | 186 | 18 | 296 | 34.12% |
| | 10 µM, 10 Days | 846 | 19 | 1597 | 2462 | 34.75% |
| | 10 µM, 10 Days | 156 | 279 | 1012 | 1447 | 20.42% |
| | 15 µM, 10 Days | 76 | 114 | 272 | 462 | 28.79% |
| CGP 57380 | 30 µM, 05 Days | 409 | 6 | 117 | 532 | 77.44% |
| | 30 µM, 05 Days | 1707 | 24 | 542 | 2273 | 75.63% |
| | 30 µM, 05 Days | 182 | 9 | 644 | 835 | 22.34% |
| | 30 µM, 05 Days | 222 | 340 | 578 | 1140 | 34.39% |
| | 30 µM, 05 Days | 544 | 6 | 376 | 926 | 59.07% |
| | 30 µM, 05 Days | 210 | 5 | 522 | 737 | 28.83% |
| | 30 µM, 10 Days | 573 | 7 | 167 | 747 | 77.18% |
| | 30 µM, 10 Days | 1619 | 63 | 447 | 2129 | 77.52% |
| | 30 µM, 10 Days | 880 | 244 | 24 | 1148 | 87.28% |
| | 30 µM, 10 Days | 520 | 2 | 603 | 1125 | 46.31% |
| Actinonin | 10 µM, 05 Days | 125 | 3 | 260 | 388 | 32.60% |
| | 10 µM, 05 Days | 728 | 10 | 653 | 1391 | 52.70% |
| | 10 µM, 10 Days | 98 | 5 | 177 | 280 | 35.89% |
| | 10 µM, 10 Days | 1168 | 42 | 927 | 2137 | 55.64% |
| | 5 µM, 05 Days | 62 | 108 | 2 | 172 | 36.63% |
| | 5 µM, 05 Days | 163 | 4 | 324 | 491 | 33.60% |

TABLE 4-continued

Additional file 4. Independent confirmatory analysis of hits from chemical screen using cells employed in HCS of LOPAC1280 library

| Chemical Name | Treatment (concentration, time) | Positive Recovery (# of cells) | No Recovery (# of cells) | Questionable Recovery (# of cells) | Number of Cells | Quantification (% rescued) |
|---|---|---|---|---|---|---|
| | 5 µM, 05 Days | 925 | 23 | 1371 | 2319 | 40.38% |
| | 5 µM, 05 Days | 2 | 55 | 1252 | 1309 | 2.25% |
| | 5 µM, 05 Days | 1 | 13 | 1571 | 1585 | 0.47% |
| | 5 µM, 05 Days | 17 | 2 | 1406 | 1425 | 1.26% |
| | 5 µM, 05 Days | 73 | 4 | 765 | 842 | 8.91% |
| | 5 µM, 10 Days | 175 | 4 | 428 | 607 | 29.16% |
| | 5 µM, 10 Days | 910 | 52 | 1271 | 2233 | 41.92% |
| | 5 µM, 10 Days | 27 | 78 | 1568 | 1673 | 3.95% |
| | 5 µM, 10 Days | 14 | 75 | 1976 | 2065 | 2.49% |
| | 5 µM, 10 Days | 185 | 1 | 858 | 1044 | 17.77% |
| Indirubin-3'-Oxime | 150 nM, 05 Days | 1 | 6 | 568 | 575 | 0.70% |
| | 150 nM, 05 Days | 173 | 16 | 1665 | 1854 | 9.76% |
| | 150 nM, 05 Days | 232 | 2 | 1910 | 2144 | 10.87% |
| | 150 nM, 10 Days | 0 | 3 | 473 | 476 | 0.32% |
| | 150 nM, 10 Days | 142 | 12 | 1573 | 1727 | 8.57% |
| | 150 nM, 10 Days | 298 | 5 | 2518 | 2821 | 10.65% |
| | 300 nM, 05 Days | 0 | 3 | 572 | 575 | 0.26% |
| | 300 nM, 05 Days | 383 | 7 | 1575 | 1972 | 19.60% |
| | 300 nM, 05 Days | 344 | 7 | 1575 | 1926 | 18.04% |
| | 300 nM, 10 Days | 2 | 4 | 548 | 554 | 0.72% |
| | 300 nM, 10 Days | 323 | 20 | 1524 | 1867 | 17.84% |
| | 300 nM, 10 Days | 1588 | 14 | 1683 | 3285 | 48.55% |
| | 300 nM, 10 Days | 99 | 351 | 276 | 726 | 37.81% |
| (R)-Roscovitine | 10 µM, 05 Days | 112 | 10 | 1099 | 1221 | 9.58% |
| | 10 µM, 10 Days | 6 | 189 | 0 | 195 | 3.08% |
| | 10 µM, 10 Days | 860 | 12 | 1416 | 2288 | 37.85% |
| | 15 µM, 05 Days | 96 | 17 | 1166 | 1279 | 8.17% |
| | 15 µM, 10 Days | 722 | 17 | 688 | 1427 | 51.19% |
| LY-294,002 hydrochloride | 10 µM, 05 Days | 158 | 140 | 30 | 328 | 52.74% |
| | 10 µM, 10 Days | 72 | 174 | 24 | 270 | 31.11% |
| | 30 µM, 10 Days | 274 | 6 | 1096 | 1376 | 20.13% |
| 1-(5-Isoquinolinyl-sulfonyl)-3-methyl-piperazine di-hydrochloride | 10 µM, 05 Days | 16 | 12 | 1568 | 1596 | 1.38% |
| | 10 µM, 10 Days | 92 | 186 | 18 | 296 | 34.12% |
| | 10 µM, 10 Days | 846 | 19 | 1597 | 2462 | 34.75% |
| | 10 µM, 10 Days | 156 | 279 | 1012 | 1447 | 20.42% |
| | 15 µM, 10 Days | 76 | 114 | 272 | 462 | 28.79% |

All cells were scored by visual inspection. '—' indicates that cells were not counted due to the absence of appreciable numbers of cells with peroxisomal rescue in the well.

CGP57380 treatment also promoted an overall robust rescue of peroxisome assembly (FIGS. 2-3); however, there was strong evidence of peroxisomal mosaicism with patches of rescued cells adjacent to patches of cells that did not show rescue. The other compounds that showed assembly rescue in over 40% of cells from the primary screen (actinonin, H-8 dihydrochloride, and indirubin-3'-oxime) showed sporadic rescue of GFP-PTS1 punctate staining and often toxicity in the follow-up experiments, which required low doses of compound to be tested. Nevertheless, evidence consistent with the ability of these compounds could promote partial rescue of peroxisome assembly was apparent (Table 4). Other compounds tested that showed at least moderate (25%) rescue of peroxisome assembly in the immortalized GFP-PTS1 expressing assay cells included LY-294,002 hydrochloride, 1-(5-Isoquinolinylsulfonyl)-3-methylpiperazine dihydrochloride, and (R)-Roscovitine (Table 4).

Figure 5A:
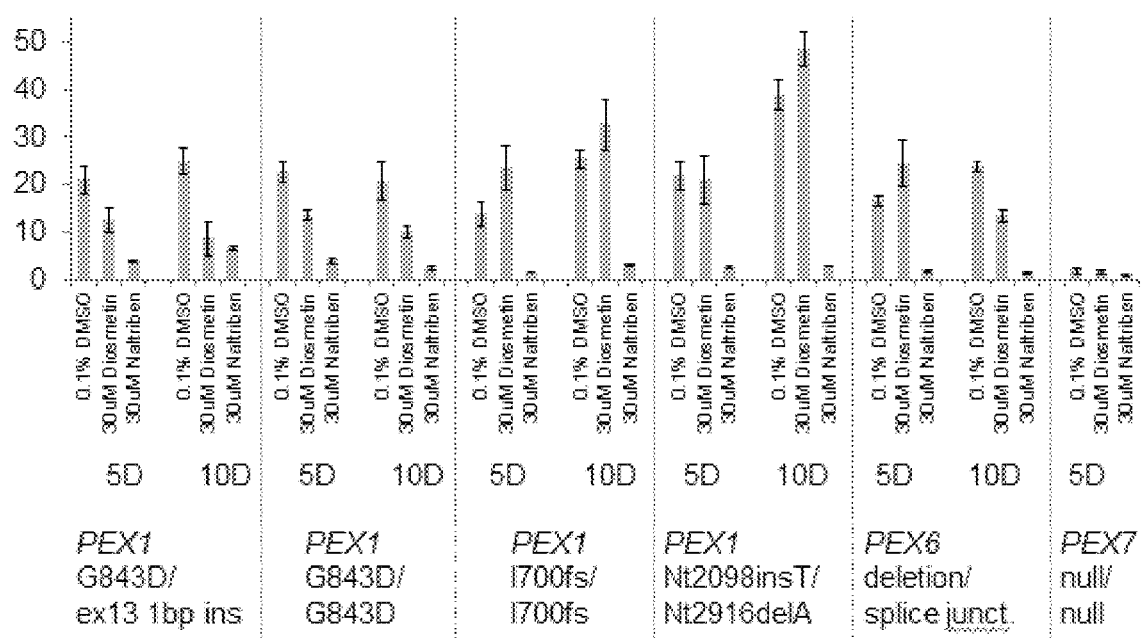
FIGS. 5A-5B: sVLCFA levels in cultured ZSD patient and control-derived fibroblasts.
Figure 5B:
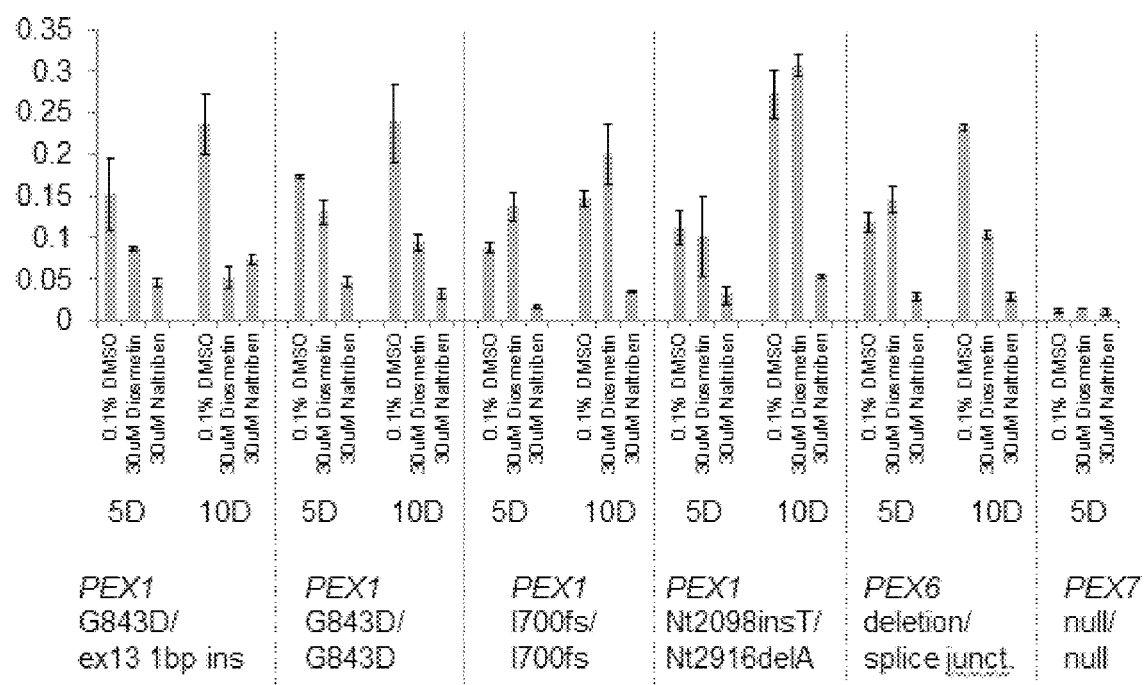

In addition, we used immunostaining was used to examine peroxisome import in primary human fibroblasts with PEX1-p.G843D/null and PEX1 null/null genotypes (FIGS. 5A-5B). As expected, cells treated with vehicle control (0.1% DMSO) showed cytoplasmic localization of either the peroxisomal matrix proteins catalase or peroxisomal thiolase and a limited numbers of peroxisomal 'ghost' membranes. Diosmetin treatment resulted in a dramatic visual rescue of catalase and thiolase import in the PEX1-p.G843D/null cells, but not cells with the PEX1 null/null genotype, consistent with its proposed role as a molecular chaperone. In contrast, naltriben treatment only showed evidence of modest rescue of thiolase, but not catalase import, in the cultured cells of either genotype.

Analysis of Lead Compound by Immunoblotting

Figure 6A:
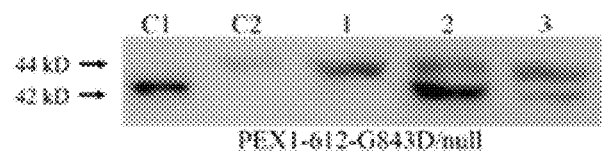
FIGS. 6A-6H: rescue of thiolase processing rescued in cultured primary fibroblasts derived from ZSD patients. Lane C1: control group with 42 kD processed thiolase from healthy donor skin fibroblast; lane C2, control group with 44 kD unprocessed thiolase from patient skin fibroblast carrying two PEX1-null alleles; lane 1, vehicle control, 0.1% DMSO treatment; lane 2, diosmetin 30 µM treatment; lane 3, naltriben 30 µM treatment. The genotypes of the patient-derived fibroblasts are provided beneath each panel.
Figure 6B:
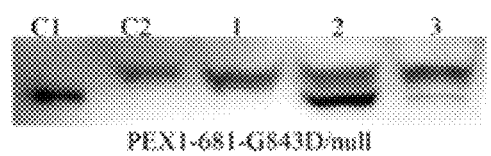
Figure 6C:
Figure 6D:
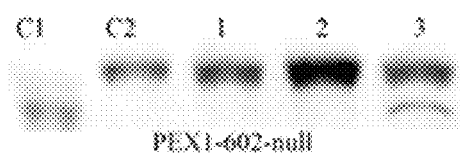
Figure 6E:
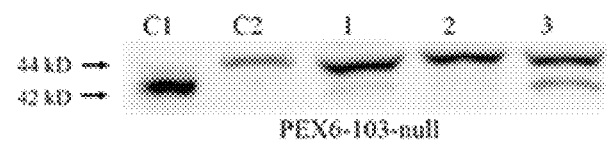
Figure 6F:
Figure 6G:
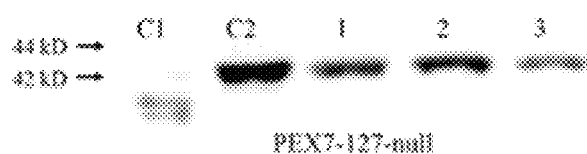
Figure 6H:
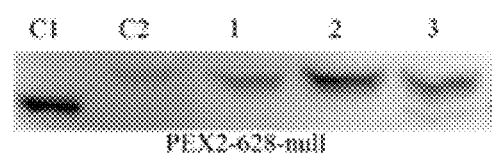

To evaluate N-terminal processing of peroxisomal thiolase upon import into the peroxisome matrix, immunoblotting of whole cell lysates from primary fibroblasts from 7 different donors including ZSD patients (FIGS. 6A-6F, 6H) and a patient with rhizomelic chondrodysplasia punctata type 1 (RCDP1), that should also have a thiolase import defect [22] was performed (FIG. 6G). Here, evidence of diosmetin showed improved thiolase processing in patient cells harboring one copy of the PEX1-p.G843D allele and in PEX26 p.R98W/p.R98W alleles, but not in the PEX1-null cell lines. In contrast, naltriben treatments provided evidence of incomplete, but substantial rescue of thiolase processing in all ZSD patient-derived cells with at least one PEX1-p.G843D allele (FIGS. 6A-6C), only null alleles for PEX1 (FIG. 6D), PEX6 (FIG. 6E), and PEX2-null mutants (FIG. 6H) as well. The PEX7-mutant cells showed no rescue of import (FIG. 6G), which is indicative of a primary defect in PTS2-import pathway alone.

Rescue of Peroxisome Biochemical Functions

Given its evidence of rescue of thiolase processing, the effects of naltriben methanesulfonate hydrate treatments on peroxisomal biochemical activities of ZSD cells were investigated. The relative and absolute levels of sVLCFA in a group of patient-derived primary fibroblasts (FIGS. 5A-5B) were evaluated. Consistent with prior reports [23], all ZSD patient skin fibroblasts showed elevated relative and absolute sVLCFA levels relative to control (skin fibroblasts-derived from an individual with PEX7 mutations expected to show normal relative sVLCFA levels). Diosmetin treatment resulted in a lowering of relative and absolute sVLCFA levels in ZSD cells either homozygous or compound heterozygous for the hypomorphic PEX1-p.G843D missense mutation at 5 and 10 days. Nevertheless, absolute and relative sVLCFA levels were increased in response to diosmetin treatments in two different ZSD-derived primary fibroblasts homozygous or compound heterozygous for two PEX1-null mutations. Evidence of sVLCFA lowering in diosmetin-treated PEX6-mutant cells treated with diosmetin was found.

In contrast, naltriben methanesulfonate hydrate treatments resulted in dramatic lowering of sVLCFA levels in all PEX1-mutant fibroblasts tested, including the PEX1-mutant ZSD patient-derived fibroblasts homozygous or compound heterozygous for null mutations with as well as the PEX6-mutant fibroblasts. Similar results were observed at 5 and 10 day treatments. This is consistent with the rescue of thiolase processing in the treated patient cells.

Discussion

Zellweger spectrum disorder (ZSD), and as used herein is a term that encompasses a heterogeneous group of autosomal recessive disorders whose peroxisomal etiology was first recognized over 40 years ago [24]. The causative role of PEX gene mutations in human PBDs was first described about twenty years ago [25, 26] with an appreciation of that the PEX1 gene is mutated in the majority of ZSD patients identified to date [27-29]. Similar to numerous other rare disorders with a well-characterized molecular etiology, current treatment options for ZSD remain largely palliative in nature [5-7]. The expanding implementation of newborn screening for ZSD and other peroxisomal disorders provides additional impetus to identify and developed more effective targeted therapies that address the molecular underpinnings of disease in the clinic [4].

To identify small molecules that can enhance peroxisome assembly and also provide novel reagents to investigate peroxisome biology, an established cell-image based HSC assay was adapted and implemented as a robust miniaturized HCS platform in 1536-well assay plates. This cell-based assay was chosen due to a number of favorable characteristics. Since the ZSD patient cells harbor the common hypomorphic PEX1-p.G843D missense and null PEX1-p.I700fs frameshift mutations, this provides an opportunity to address the molecular basis for disease in the largest segment of the ZSD patient population. Furthermore, the cell-image based assay provides an opportunity to identify compounds that promote peroxisome assembly by any mechanism. Given its successful implementation in 96-well assay plates [8], the miniaturization provides an opportunity to interrogate larger chemical libraries in a more cost-effective manner to investigate responses to multiple doses of each compound assayed. Imaging techniques well known in the art can be used to determine whether peroxisome assembly is being enhanced or promoted in a cell or a subject and techniques for such are described herein. Thus, one of skill in the art can determine if peroxisome assembly has been improved or dysfunction alleviated by, for example visual inspection based on the clarity of cytoplasmic staining and the appearance of cells with at least 7 distinct punctate cytoplasmic structures consistent with peroxisome size and shape. In one aspect, treated population of cells have at least 30% of cells with rescue of peroxisome assembly.

In the initial screen of the Sigma LOPAC1280 chemical library, a group of eight compounds with rescue of peroxisome assembly in over 50% of patient cells treated with the highest concentration of drug was identified. Taking advantage of the 7 point titration of every compound, enhanced peroxisome assembly in substantive numbers of cells, as evidenced by the appearance of punctate GFP-PTS1 structures, was not observed in response to treatment with submicromolar concentrations of this library at the two day timeframe.

Initial validation steps involved retesting 'hit' compounds in the same immortalized ZSD patient fibroblasts used in HCS of the LOPAC1280 library. Robust rescue of peroxisome assembly, as shown by punctate GFP-PTS1 signals, was demonstrated for naltriben methanesulfonate hydrate, naltrindole hydrochloride, and CGP57380. The other compounds tested also demonstrated evidence of improved peroxisome assembly, including actinonin, H-8 dihydrochloride, and indirubin-3'-oxime. Importantly, a flavonoid compound known to improve peroxisome assembly in ZSD cells harboring at least one PEX1-p.G843D allele (Braverman, personal communication) was independently identified in this screen in a blinded manner.

Figure 7A:
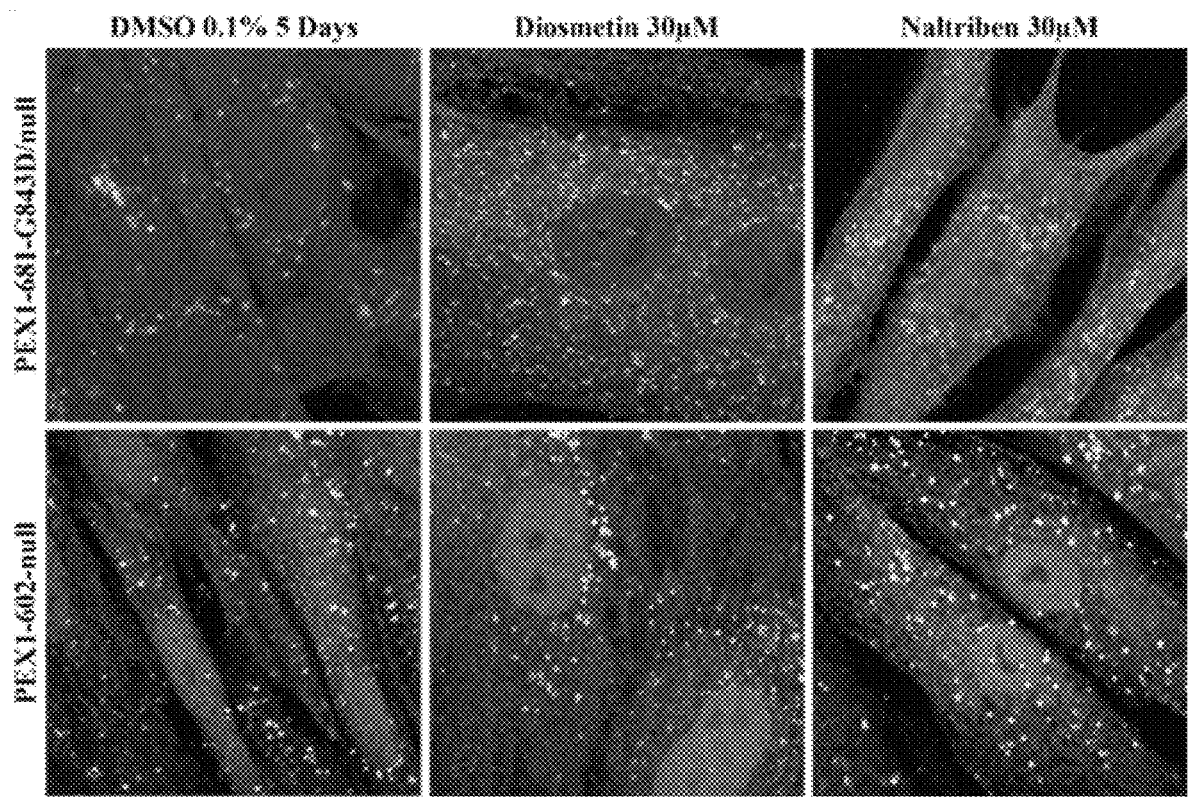
FIGS. 7A-7B: peroxisome assembly in primary fibroblasts. Primary fibroblast cells were cultured for 5 days in the presences of the indicated compounds and subject to immunostaining. The upper and lower panels in FIGS. 7A-7B consistent of patient-derived fibroblasts with PEX1-p.G843D/null and PEX1-null/null genotypes, respectively.
Figure 7B:
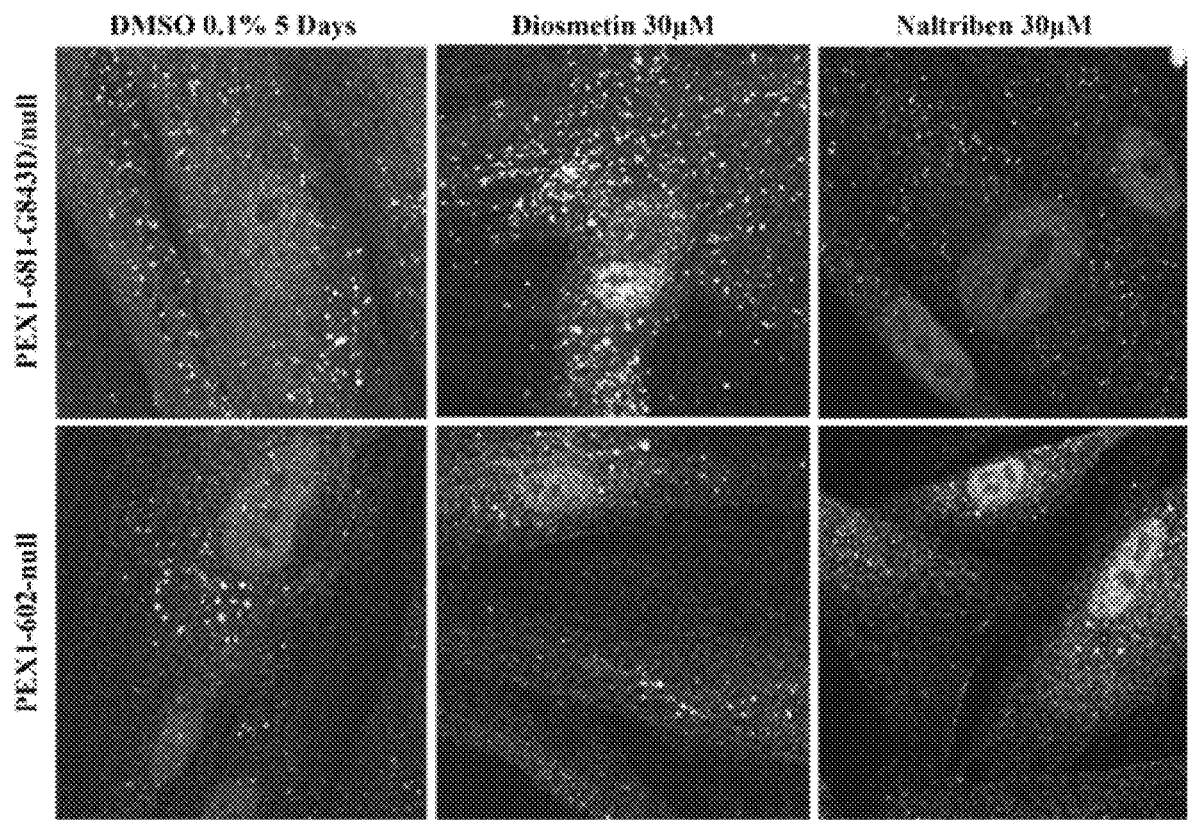

The compound naltriben methanesulfonate hydrate was chosen for most intensive analysis in primary ZSD cells of various genotypes by cell immunostaining (FIGS. 7A-7B), analysis of peroxisomal thiolase processing (FIGS. 6A-6H), and biochemical analysis of relative and absolute sVCLFA levels (FIGS. 5A-5B). Again, in agreement with prior observations, diosmetin treatments lead to a robust rescue of peroxisome assembly in cells with PEX1-p.G843D alleles. Surprisingly, evidence of improved thiolase processing in ZSD patient cells treated with naltriben methanesulfonate hydrate not only carrying PEX1-p.G843D alleles, but also those homozygous or compound heterozygous for null alleles for PEX1, PEX2, and PEX6 was found (FIGS. 7A-7B). In the case of null alleles, peroxisome thiolase import was close to 10%, which indicates relatively minor rescue.

As a more direct functional assay of peroxisomal activities, relative and absolute VLCFA levels were measured in ZSD donor-derived primary fibroblasts treated with diosmetin and naltriben methanesulfonate hydrate. In agreement, with the thiolase processing assays naltriben methanesulfonate hydrate treatments resulted in a dramatic lowering to relative and absolute sVLCFA levels in ZSD cells harboring PEX1-p.G843D alleles or null PEX1 or PEX6 alleles. Similar results were found in pilot studies involving the structurally similar naltrindole hydrochloride and CGP57380 compounds.

Figure 8:
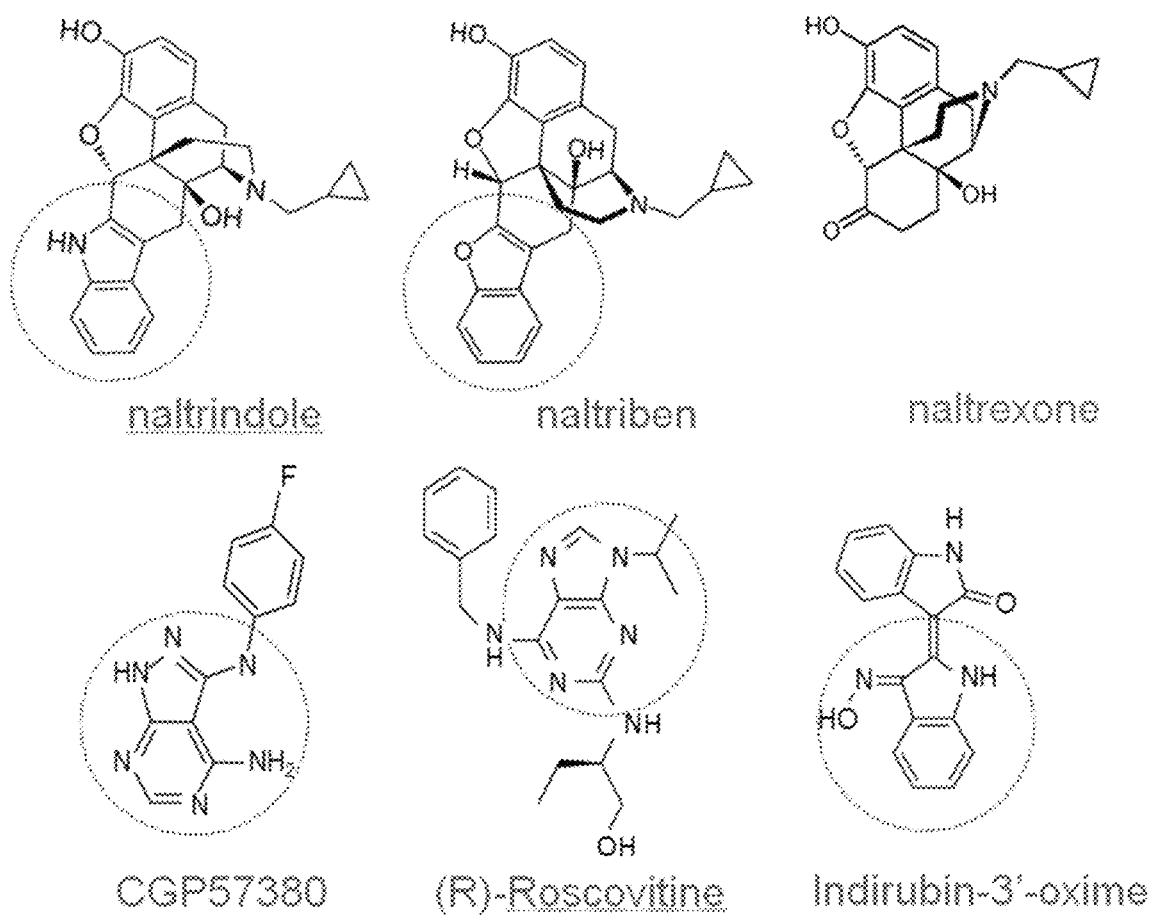
FIG. 8: chemical structures of active compounds uncovered in the HCS that showed a similar structural motif. Naltrexone (red) did not show activity in the chemical screen and is provided to highlight the shared structural motif absence of this structural motif in a related, but non-active compound. The names of the active compounds are provided in green.

The mechanistic basis for the rescue of peroxisomal functions in the ZSD-derived cells treated with naltriben methanesulfonate hydrate, naltrindole hydrochloride, and CGP57380 are unknown. As a means of interrogating these functional aspects of these small molecules, the activity of the structurally similar FDA-approved drug naltrexone was investigated and no evidence of peroxisome activity was found. This indicates the potential functional importance of the highlighted chemical moiety in FIG. 8 that is shared by the molecules naltriben methanesulfonate hydrate, naltrindole, CGP57380, (R)-Roscovitine, and indirubin-3'-oxime that showed activity in the initial HCS screen and in follow-up functional assays when conducted (Table 3).

Of special importance, naltriben methanesulfonate hydrate and naltrindole hydrochloride are brain permeable opioid receptor antagonists that are used in studies of chemical addiction in rodents [30, 31]. CGP57380 is a cell-permeable selective inhibitor of mitogen-activated protein kinase-interacting kinase 1 (MNK1) [32], whose brain permeability has not been reported. Nevertheless, the brain permeability of naltriben methanesulfonate hydrate and naltrindole hydrochloride is an intriguing property of these compounds given the neurological aspects of ZSD.

Unraveling the mechanistic basis for rescue of peroxisome assembly by the compounds highlighted in this study can be challenging and is dependent upon the mode of activity. As discussed the pilot HCS uncovered molecules previously shown to bind the ATP binding site of ABC transporter proteins [8]. Coupled with prior observations that PEX1-p.G843D is a temperature-sensitive allele and responds to other potential molecular chaperones [9, 14], it was proposed that the misfolded PEX1-p.G843D allele protein is amenable to molecular chaperone therapy. Nevertheless, the ability of naltriben methanesulfonate hydrate to rescue peroxisome assembly in cells that are incapable of producing PEX1, PEX6, or PEX2 protein indicates a differing mode of activity from previously discovered compounds, including diosmetin whose activity is proposed to be a molecular chaperone (Braverman et al. in preparation). The development of in vitro peroxisome assembly assays [33-35] can provide valuable tools for investigations into whether there are direct interactions with the peroxisome assembly machinery. Other lines of investigation involving transcriptomic or proteomic investigations will also be of value, but their utility is highly dependent upon the number of molecular changes observed that could potentially mask molecular pathways of greatest importance to the rescue of peroxisome assembly.

Investigations into structure-activity relationships for the confirmed hits could potentially generate a set of lead compounds that can be studied in emerging induced pluripotent stem cell (iPSC) models [16] and genetically engineered mouse models [36], especially the PEX1-p.G844D model of mild ZSD [37], and other invertebrate models [38]. In addition, the elucidation of their mechanism of activity can lead into valuable insights into peroxisome structure, function, replication, and cellular homeostasis. Small molecules detected in such screens can have potential for more common diseases, including diabetes [39] and Alzheimer's disease [40].

Methods

In one aspect, provided herein is a method of treating Zellweger spectrum disorder and/or diseases associated with peroxisome dysfunction in a subject in need thereof comprising administering to the subject a therapeutically effective amount of a compound of Formula I:

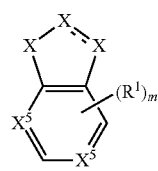

Formula I or a tautomer thereof, or a pharmaceutically acceptable salt of each of the foregoing, or an N-oxide of each of the foregoing, or a pharmaceutically acceptable solvate of each of the foregoing, wherein ⚞ is a single or a double bond;
X is $NR^2$ or $CR^5R^5$ when ⚞ is a single bond or X is N or $CR^5$ when ⚞ is a double bond;
$X^5$ is N or $CR^5$, provided that at least one of X and $X^5$ is N or $NR^2$;
each $R^2$ independently is H, an optionally substituted $C_1$-$C_8$ alkyl, an optionally substituted $C_1$-$C_8$ alkoxy, or an optionally substituted $C_2$-$C_8$ alkenyl;
each $R^5$ independently is H, an optionally substituted $C_1$-$C_8$ alkyl, an optionally substituted $C_1$-$C_8$ alkoxy, an optionally substituted $C_2$-$C_8$ alkenyl, an optionally substituted =$NR^6$, or an optionally substituted —$NR^{20}R^{30}$;
each $R^1$ independently is H, an optionally substituted $C_1$-$C_8$ alkyl, an optionally substituted $C_1$-$C_8$ alkoxy; or an optionally substituted —$NR^{20}R^{30}$;
each $R^{20}$ and $R^{30}$ independently is H, an optionally substituted $C_1$-$C_8$ alkyl, an optionally substituted $C_1$-$C_8$ alkoxy, an optionally substituted 5-10 membered aryl, an optionally substituted 5-10 membered heteroaryl; an optionally substituted 3-10 membered cycloalkyl, or an optionally substituted 5-10 membered heterocyclyl;
each $R^6$ independently is H, an optionally substituted $C_1$-$C_8$ alkyl, an optionally substituted $C_1$-$C_8$ alkoxy, or hydroxy; and
m is 0, 1, or 2.

In some embodiments, the Zellweger spectrum is caused by a PEX gene mutation.

In some embodiments, the PEX gene mutation causes abnormal peroxisome assembly.

In a further aspect, the subject is a mammal, e.g. a human, and has at least one PEX1-p.G843D allele, and in another aspect, the subject has two null PEX1 alleles.

In another aspect, provided herein is a method of treating Zellweger spectrum disorder and/or diseases associated with peroxisome dysfunction in a subject in need thereof comprising administering to the subject a therapeutically effective amount of a compound of Formula II:

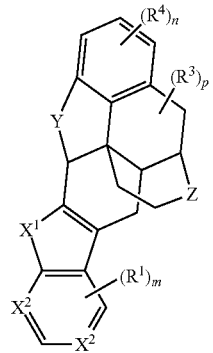

Formula II or a tautomer thereof, or a pharmaceutically acceptable salt of each of the foregoing, or an N-oxide of each of the foregoing, or a pharmaceutically acceptable solvate of each of the foregoing, wherein $X^1$ is O, S, or $NR^2$;
$X^2$ is N or $CR^5$;
each $R^1$ independently is H, an optionally substituted $C_1$-$C_8$ alkyl, an optionally substituted $C_1$-$C_8$ alkoxy; or an optionally substituted —$NR^{20}NR^{30}$;
each $R^2$ independently is H, an optionally substituted $C_1$-$C_8$ alkyl, an optionally substituted $C_1$-$C_8$ alkoxy, or an optionally substituted $C_2$-$C_8$ alkenyl;

each R[5] independently is H, an optionally substituted $C_1$-$C_8$ alkyl, an optionally substituted $C_1$-$C_8$ alkoxy, an optionally substituted $C_2$-$C_8$ alkenyl, an optionally substituted =NR[6], or an optionally substituted —NR[20]R[30];

each R[20] and R[30] independently is H, an optionally substituted $C_1$-$C_8$ alkyl, an optionally substituted $C_1$-$C_8$ alkoxy, an optionally substituted 5-10 membered aryl, an optionally substituted 5-10 membered heteroaryl, an optionally substituted 3-10 membered cycloalkyl, or an optionally substituted 5-10 membered heterocyclyl;

each R[3] and R[4] independently is H, an optionally substituted $C_1$-$C_8$ alkyl, an optionally substituted $C_1$-$C_8$ alkoxy; an optionally substituted $C_2$-$C_8$ alkenyl, or a hydroxy;

Y and Z independently is O, S, or NR[2];

n is 0, 1, 2, or 3;

m is 0, 1, or 2; and p is 0, 1, 2, or 3.

In some embodiments, the Zellweger spectrum is caused by a PEX gene mutation.

In some embodiments, the PEX gene mutation causes abnormal peroxisome assembly.

In a further aspect, the subject is a mammal, e.g. a human, and has at least one PEX1-p.G843D allele, and in another aspect, the subject has two null PEX1 alleles.

In some embodiments, the compound is naltriben or naltrindole. In some embodiments, the compound is naltriben methanesulfonate hydrate. In some embodiments, the compound is naltrindole hydrochloride.

In one aspect, provided herein is a method of treating Zellweger spectrum disorder and/or diseases associated with peroxisome dysfunction in a subject in need thereof comprising administering to the subject a therapeutically effective amount of a compound of Table 3, or a tautomer thereof, or a pharmaceutically acceptable salt of each of the foregoing, or an N-oxide of each of the foregoing, or a pharmaceutically acceptable solvate of each of the foregoing.

In some embodiments, the Zellweger spectrum is caused by a PEX gene mutation.

In some embodiments, the PEX gene mutation causes abnormal peroxisome assembly.

In some embodiments, the compound is naltriben or naltrindole. In some embodiments, the compound is naltriben methanesulfonate hydrate. In some embodiments, the compound is naltrindole hydrochloride.

In a further aspect, the subject is a mammal, e.g. a human, and has at least one PEX1-p.G843D allele, and in another aspect, the subject has two null PEX1 alleles.

In one aspect, provided herein is a method of improving peroxisome assembly in a cell in need thereof comprising administering to the cell a therapeutically effective amount of a compound of Formula I:

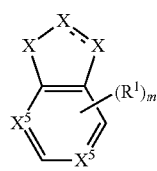

Formula I or a tautomer thereof, or a pharmaceutically acceptable salt of each of the foregoing, or an N-oxide of each of the foregoing, or a pharmaceutically acceptable solvate of each of the foregoing, wherein:

⟋⟋ is a single or a double bond;

X is NR[2] or CR[5]R[5] when ⟋⟋ is a single bond or X is N or CR[5] when ⟋⟋ is a double bond;

X[5] is N or CR[5], provided that at least one of X and X[5] is N or NR[2];

each R[2] independently is H, an optionally substituted $C_1$-$C_8$ alkyl, an optionally substituted $C_1$-$C_8$ alkoxy, or an optionally substituted $C_2$-$C_8$ alkenyl;

each R[5] independently is H, an optionally substituted $C_1$-$C_8$ alkyl, an optionally substituted $C_1$-$C_8$ alkoxy, an optionally substituted $C_2$-$C_8$ alkenyl, an optionally substituted =NR[6], or an optionally substituted —NR[20]R[30];

each R[1] independently is H, an optionally substituted $C_1$-$C_8$ alkyl, an optionally substituted $C_1$-$C_8$ alkoxy; or an optionally substituted —NR[20]R[30];

each R[20] and R[30] independently is H, an optionally substituted $C_1$-$C_8$ alkyl, an optionally substituted $C_1$-$C_8$ alkoxy, an optionally substituted 5-10 membered aryl, an optionally substituted 5-10 membered heteroaryl; an optionally substituted 3-10 membered cycloalkyl, or an optionally substituted 5-10 membered heterocyclyl;

each R[6] independently is H, an optionally substituted $C_1$-$C_8$ alkyl, an optionally substituted $C_1$-$C_8$ alkoxy, or hydroxy; and m is 0, 1, or 2.

In a further aspect, the cell is a mammal cell, e.g. a human cell, and has at least one PEX1-p.G843D allele, and in another aspect, the subject has two null PEX1 alleles.

In some embodiments, the peroxisome assembly is improved by from about 20% to about 96%. In some embodiments, the peroxisome assembly is improved by at least 20%. In some embodiments, the peroxisome assembly is improved by at least 40%. In some embodiments, the peroxisome assembly is improved by at least 50%. The methods to determine % improvement of a peroxisome in a cell or population of cells is known in the art and described above.

In another aspect, provided herein is a method of improving peroxisome assembly in a cell in need thereof comprising administering to the cell a therapeutically effective amount of a compound of Formula II:

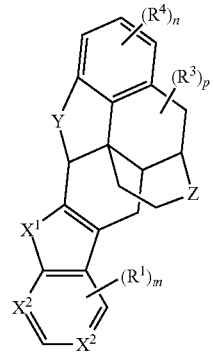

Formula II or a tautomer thereof, or a pharmaceutically acceptable salt of each of the foregoing, or an N-oxide of each of the foregoing, or a pharmaceutically acceptable solvate of each of the foregoing, wherein X[1] is O, S, or NR[2];

X[2] is N or CR[5];

each R[1] independently is H, an optionally substituted $C_1$-$C_8$ alkyl, an optionally substituted $C_1$-$C_8$ alkoxy; or an optionally substituted —NR[20]NR[30];

each $R^2$ independently is H, an optionally substituted $C_1$-$C_8$ alkyl, an optionally substituted $C_1$-$C_8$ alkoxy, or an optionally substituted $C_2$-$C_8$ alkenyl;

each $R^5$ independently is H, an optionally substituted $C_1$-$C_8$ alkyl, an optionally substituted $C_1$-$C_8$ alkoxy, an optionally substituted $C_2$-$C_8$ alkenyl, an optionally substituted =$NR^6$, or an optionally substituted —$NR^{20}R^{30}$;

each $R^{20}$ and $R^{30}$ independently is H, an optionally substituted $C_1$-$C_8$ alkyl, an optionally substituted $C_1$-$C_8$ alkoxy, an optionally substituted 5-10 membered aryl, an optionally substituted 5-10 membered heteroaryl, an optionally substituted 3-10 membered cycloalkyl, or an optionally substituted 5-10 membered heterocyclyl;

each $R^3$ and $R^4$ independently is H, an optionally substituted $C_1$-$C_8$ alkyl, an optionally substituted $C_1$-$C_8$ alkoxy; an optionally substituted $C_2$-$C_8$ alkenyl, or a hydroxy;

Y and Z independently is O, S, or $NR^2$;

n is 0, 1, 2, or 3;

m is 0, 1, or 2; and p is 0, 1, 2, or 3.

In some embodiments, the peroxisome assembly is improved by from about 20% to about 96%. In some embodiments, the peroxisome assembly is improved by at least 20%. In some embodiments, the peroxisome assembly is improved by at least 40%. In some embodiments, the peroxisome assembly is improved by at least 50%. The methods to determine % improvement of a peroxisome in a cell or population of cells is known in the art and described above.

In a further aspect, the cell is a mammal cell, e.g. a human cell, and has at least one PEX1-p.G843D allele, and in another aspect, the cell has two null PEX1 alleles.

In some embodiments, the compound is naltriben or naltrindole. In some embodiments, the compound is naltriben methanesulfonate hydrate. In some embodiments, the compound is naltrindole hydrochloride.

In another aspect, provided herein is a method of improving peroxisome assembly in a cell in need thereof comprising administering to the cell a therapeutically effective amount of a compound of Table 3, or a tautomer thereof, or a pharmaceutically acceptable salt of each of the foregoing, or an N-oxide of each of the foregoing, or a pharmaceutically acceptable solvate of each of the foregoing. In one aspect, the cell is a mammal cell, e.g. a human cell, and has at least one PEX1-p.G843D allele, and in another aspect, the cell has two null PEX1 alleles.

In some embodiments, the peroxisome assembly is improved by from about 20% to about 96%. In some embodiments, the peroxisome assembly is improved by at least 20%. In some embodiments, the peroxisome assembly is improved by at least 40%. In some embodiments, the peroxisome assembly is improved by at least 50%. The methods to determine % improvement of a peroxisome in a cell or population of cells is known in the art and described above.

In some embodiments, the compound is naltriben or naltrindole. In some embodiments, the compound is naltriben methanesulfonate hydrate. In some embodiments, the compound is naltrindole hydrochloride.

In some embodiments, the methods provided herein further comprise detecting for the presence of the PEX gene mutation in a sample isolated from the subject or in a cell or population of cells prior to administration of the compound of Formula I, a compound of Formula II, a compound of Table 3, or a tautomer thereof, or a pharmaceutically acceptable salt of each of the foregoing, or an N-oxide of each of the foregoing, or a pharmaceutically acceptable solvate of each of the foregoing.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

REFERENCES

1. Steinberg S J, Raymond G V, Braverman N E, Moser A B. Peroxisome Biogenesis Disorders, Zellweger Syndrome Spectrum. In: Pagon R A, Adam M P, Ardinger H H, Bird T D, Dolan C R, Fong C T et al., editors. GeneReviews(R). Seattle (Wash.) 1993.
2. Wanders R J, Waterham H R. Biochemistry of mammalian peroxisomes revisited. Annu Rev Biochem. 2006; 75:295-332.
3. Wanders R J. Metabolic functions of peroxisomes in health and disease. Biochimie. 2014; 98:36-44.
4. Braverman N E, D'Agostino M D, Maclean G E. Peroxisome biogenesis disorders: Biological, clinical and pathophysiological perspectives. Dev Disabil Res Rev. 2013; 17:187-96.
5. Poll-The B T, Gartner J. Clinical diagnosis, biochemical findings and MRI spectrum of peroxisomal disorders. Biochim Biophys Acta. 2012; 1822:1421-9.
6. Klouwer F C, Berendse K, Ferdinandusse S, Wanders R J, Engelen M, Poll-The B T. Zellweger spectrum disorders: clinical overview and management approach. Orphanet J Rare Dis. 2015; 10:151.
7. Braverman N E, Raymond G V, Rizzo W B, Moser A B, Wilkinson M E, Stone E M et al. Peroxisome biogenesis disorders in the Zellweger spectrum: An overview of current diagnosis, clinical manifestations, and treatment guidelines. Mol Genet Metab. 2016; 117:313-21.
8. Zhang R, Chen L, Jiralerspong S, Snowden A, Steinberg S, Braverman N. Recovery of PEX1-Gly843Asp peroxisome dysfunction by small-molecule compounds. Proc Natl Acad Sci USA. 2010; 107:5569-74.
9. Walter C, Gootjes J, Mooijer P A, Portsteffen H, Klein C, Waterham H R et al. Disorders of peroxisome biogenesis due to mutations in PEX1: phenotypes and PEX1 protein levels. Am J Hum Genet. 2001; 69:35-48.
10. Poll-The B T, Gootjes J, Duran M, De Klerk J B, Wenniger-Prick L J, Admiraal R J et al. Peroxisome biogenesis disorders with prolonged survival: phenotypic expression in a cohort of 31 patients. Am J Med Genet A. 2004; 126A:333-8.
11. Majewski J, Wang Z, Lopez I, Al Humaid S, Ren H, Racine J et al. A new ocular phenotype associated with an unexpected but known systemic disorder and mutation: novel use of genomic diagnostics and exome sequencing. J Med Genet. 2011; 48:593-6.
12. Lu H, Chang D J, Baratte B, Meijer L, Schulze-Gahmen U. Crystal structure of a human cyclin-dependent kinase 6 complex with a flavonol inhibitor, fisetin. J Med Chem. 2005; 48:737-43.
13. Katayama K, Masuyama K, Yoshioka S, Hasegawa H, Mitsuhashi J, Sugimoto Y. Flavonoids inhibit breast cancer resistance protein-mediated drug resistance: transporter specificity and structure-activity relationship. Cancer Chemother Pharmacol. 2007; 60:789-97.
14. Berendse K, Ebberink M S, Ijlst L, Poll-The B T, Wanders R J, Waterham H R. Arginine improves peroxisome functioning in cells from patients with a mild peroxisome biogenesis disorder. Orphanet J Rare Dis. 2013; 8:138.
15. Urban D J, Zheng W, Goker-Alpan O, Jadhav A, Lamarca M E, Inglese J et al. Optimization and validation of two miniaturized glucocerebrosidase enzyme assays for high throughput screening. Comb Chem High Throughput Screen. 2008; 11:817-24.
16. Wang X M, Yik W Y, Zhang P, Lu W, Huang N, Kim B R et al. Induced pluripotent stem cell models of Zellweger spectrum disorder show impaired peroxisome assembly and cell type-specific lipid abnormalities. Stem Cell Res Ther. 2015; 6:158.
17. Wang X M, Yik W Y, Zhang P, Lu W, Dranchak P K, Shibata D et al. The gene expression profiles of induced pluripotent stem cells from individuals with childhood cerebral adrenoleukodystrophy are consistent with proposed mechanisms of pathogenesis. Stem Cell Res Ther. 2012; 3:39.
18. Karaman M W, Houck M L, Chemnick L G, Nagpal S, Chawannakul D, Sudano D et al. Comparative analysis of gene-expression patterns in human and african great ape cultured fibroblasts. Genome Res. 2003; 13:1619-30.
19. Dranchak P K, Di Pietro E, Snowden A, Oesch N, Braverman N E, Steinberg S J et al. Nonsense suppressor therapies rescue peroxisome lipid metabolism and assembly in cells from patients with specific PEX gene mutations. Journal of Cellular Biochemistry. 2010.
20. Goonoo N, Bhaw-Luximon A, Ujoodha R, Jhugroo A, Hulse G K, Jhurry D. Naltrexone: a review of existing sustained drug delivery systems and emerging nano-based systems. J Control Release. 2014; 183:154-66.
21. Garbutt J C, Greenblatt A M, West S L, Morgan L C, Kampov-Polevoy A, Jordan H S et al. Clinical and biological moderators of response to naltrexone in alcohol dependence: a systematic review of the evidence. Addiction. 2014; 109:1274-84.
22. Braverman N E, Moser A B, Steinberg S J. Rhizomelic Chondrodysplasia *Punctata* Type 1. In: Pagon R A, Adam M P, Ardinger H H, Wallace S E, Amemiya A, Bean L J H et al., editors. GeneReviews(R). Seattle (Wash.) 1993.
23. Steinberg S J, Dodt G, Raymond G V, Braverman N E, Moser A B, Moser H W. Peroxisome biogenesis disorders. Biochim Biophys Acta. 2006; 1763:1733-48.
24. Goldfischer S, Moore C L, Johnson A B, Spiro A J, Valsamis M P, Wisniewski H K et al. Peroxisomal and mitochondrial defects in the cerebro-hepato-renal syndrome. Science. 1973; 182:62-4.
25. Reuber B E, Germain-Lee E, Collins C S, Morrell J C, Ameritunga R, Moser H W et al. Mutations in PEX1 are the most common cause of peroxisome biogenesis disorders. Nat Genet. 1997; 17:445-8.
26. Braverman N, Steel G, Obie C, Moser A, Moser H, Gould S J et al. Human PEX7 encodes the peroxisomal PTS2 receptor and is responsible for rhizomelic chondrodysplasia punctata. Nat Genet. 1997; 15:369-76.
27. Yik W Y, Steinberg S J, Moser A B, Moser H W, Hacia J G. Identification of novel mutations and sequence variation in the Zellweger syndrome spectrum of peroxisome biogenesis disorders. Hum Mutat. 2009; 30:E467-80.
28. Steinberg S, Chen L, Wei L, Moser A, Moser H, Cutting G et al. The PEX Gene Screen: molecular diagnosis of peroxisome biogenesis disorders in the Zellweger syndrome spectrum. Mol Genet Metab. 2004; 83:252-63.
29. Rosewich H, Ohlenbusch A, Gartner J. Genetic and clinical aspects of Zellweger spectrum patients with PEX1 mutations. J Med Genet. 2005; 42:e58.
30. Fenalti G, Giguere P M, Katritch V, Huang X P, Thompson A A, Cherezov V et al. Molecular control of delta-opioid receptor signalling. Nature. 2014; 506:191-6.
31. Beaudry H, Gendron L, Moron J A. Implication of delta opioid receptor subtype 2 but not delta opioid receptor subtype 1 in the development of morphine analgesic tolerance in a rat model of chronic inflammatory pain. Eur J Neurosci. 2015; 41:901-7.
32. Grzmil M, Huber R M, Hess D, Frank S, Hynx D, Moncayo G et al. MNK1 pathway activity maintains protein synthesis in rapalog-treated gliomas. J Clin Invest. 2014; 124:742-54.
33. Gardner B M, Chowdhury S, Lander G C, Martin A. The Pex1/Pex6 complex is a heterohexameric AAA+motor with alternating and highly coordinated subunits. J Mol Biol. 2015; 427:1375-88.
34. Blok N B, Tan D, Wang R Y, Penczek P A, Baker D, DiMaio F et al. Unique double-ring structure of the peroxisomal Pex1/Pex6 ATPase complex revealed by cryo-electron microscopy. Proc Natl Acad Sci USA. 2015; 112:E4017-25.
35. Tan D, Blok N B, Rapoport T A, Walz T. Structures of the double-ring AAA ATPase Pex1-Pex6 involved in peroxisome biogenesis. FEBS J. 2016; 283:986-92.
36. Baes M, Van Veldhoven P P. Mouse models for peroxisome biogenesis defects and beta-oxidation enzyme deficiencies. Biochim Biophys Acta. 2012; 1822:1489-500.

37. Hiebler S, Masuda T, Hacia J G, Moser A B, Faust P L, Liu A et al. The Pex1-G844D mouse: a model for mild human Zellweger spectrum disorder. Mol Genet Metab. 2014; 111:522-32.
38. Van Veldhoven P P, Baes M. Peroxisome deficient invertebrate and vertebrate animal models. Front Physiol. 2013; 4:335.
39. Sexton J Z, He Q, Forsberg L J, Brenman J E. High content screening for non-classical peroxisome proliferators. Int J High Throughput Screen. 2010; 2010:127-40.
40. Dorninger F, Brodde A, Braverman N E, Moser A B, Just W W, Forss-Petter S et al. Homeostasis of phospholipids—The level of phosphatidylethanolamine tightly adapts to changes in ethanolamine plasmalogens. Biochimica Et Biophysica Acta-Molecular and Cell Biology of Lipids. 2015; 1851:117-28.

What is claimed is:

1. A method of treating Zellweger spectrum disorder comprising Zellweger Syndrome (ZS), neonatal adrenoleukodystrophy, or Refsum disease (IRD), in a subject in need thereof comprising administering to the subject a therapeutically effective amount of a compound selected from naltriben, naltrindole, or a tautomer of each thereof, or a pharmaceutically acceptable salt of each of the foregoing.

2. The method of claim 1, wherein the Zellweger spectrum disorder is caused by a PEX gene mutation.

3. The method of claim 2, wherein the PEX gene mutation causes abnormal peroxisome assembly.

4. The method of claim 1, wherein the compound is naltriben or naltrindole.

5. The method of claim 1, wherein the compound is naltriben methanesulfonate hydrate.

6. The method of claim 1, wherein the compound is naltrindole hydrochloride.

7. A method of improving peroxisome assembly in a cell in need thereof comprising administering to the cell a therapeutically effective amount of a compound selected from naltriben, naltrindole,
   or a tautomer of each thereof, or a pharmaceutically acceptable salt of each of the foregoing.

8. The method of claim 7, wherein the peroxisome assembly is improved by from about 20% to about 96%.

9. The method of claim 7, wherein the peroxisome assembly is improved by at least 20%.

10. The method of claim 7, wherein the peroxisome assembly is improved by at least 40%.

11. The method of claim 7, wherein the peroxisome assembly is improved by at least 50%.

12. The method of claim 7, wherein the compound is naltriben or naltrindole.

13. The method of claim 7, wherein the compound is naltriben methanesulfonate hydrate.

14. The method of claim 7, wherein the compound is naltrindole hydrochloride.

15. The method of claim 1, further comprising detecting for the presence of the PEX gene mutation in a sample isolated from the subject prior to administration of the compound or a tautomer thereof, or a pharmaceutically acceptable salt of each of the foregoing.

16. The method of claim 1, wherein the Zellweger spectrum disorder is caused by a misfolded PEX1 protein.

* * * * *